United States Patent
Dang et al.

(10) Patent No.: US 6,403,675 B1
(45) Date of Patent: Jun. 11, 2002

(54) BIODEGRADABLE COMPOSITIONS COMPRISING POLY(CYCLOALIPHATIC PHOSPHOESTER) COMPOUNDS, ARTICLES, AND METHODS FOR USING THE SAME

(75) Inventors: Wenbin Dang, Ellicott City; Hai-quan Mao, Towson; Irina Kadiyala, Baltimore; Kam W. Leong; Zhong Zhao, both of Ellicott City, all of MD (US); James P. English, Chelsea, AL (US)

(73) Assignees: Guilford Pharmaceuticals, Inc.; Johns Hopkins University, both of Baltimore, MD (US)

( * ) Notice: Subject to any disclaimer, the term of this patent is extended or adjusted under 35 U.S.C. 154(b) by 0 days.

(21) Appl. No.: 09/070,204

(22) Filed: Apr. 30, 1998

Related U.S. Application Data

(63) Continuation-in-part of application No. 08/841,345, filed on Apr. 30, 1997, now abandoned.

(51) Int. Cl.$^7$ .......................... A61K 31/80; C08G 79/04
(52) U.S. Cl. ....................... 523/113; 523/111; 523/124; 524/610; 528/359; 528/356; 528/400; 424/486; 424/78.08; 623/1
(58) Field of Search .................................. 523/113, 111; 524/610; 528/354, 356, 400; 424/486, 78.08; 623/1

(56) References Cited

U.S. PATENT DOCUMENTS

| | | | |
|---|---|---|---|
| 3,271,329 A | | 9/1966 | Coover et al. .............. 528/167 |
| 3,520,849 A | | 7/1970 | Vandenberg et al. ........ 528/244 |
| 4,315,969 A | * | 2/1982 | Login et al. ................. 524/610 |
| 4,328,174 A | | 5/1982 | Schmidt et al. ............. 528/167 |
| 4,374,971 A | | 2/1983 | Schmidt et al. ............. 528/167 |
| 5,219,564 A | | 6/1993 | Zalipsky et al. .......... 428/78.17 |
| 5,530,093 A | | 6/1996 | Engelhardt et al. | |
| 5,620,700 A | * | 4/1997 | Berggren et al. | |
| 5,626,862 A | * | 5/1997 | Brem et al. | |
| 6,166,173 A | * | 12/2000 | Mao et al. .................. 523/113 |

FOREIGN PATENT DOCUMENTS

EP 0386757 12/1990

OTHER PUBLICATIONS

Pretula, "High–molecular–weight Poly(alkylene phosphonate)s by Condensation of Dialkylphosphonates with Diols", *Die Makromolekulare Chemie*, 191:3, 371–80 (1990).
Leong et al., "Polymeric Controlled Drug Delivery", *Advanced Drug Delivery Rev.*, 1:199–233 (1987).
Langer, "New Methods of Drug Delivery", *Science*, 249:1527–33 (1990).
Pulapura et al., "Trends in the Development of Bioresorbable Polymers for Medical Applications", *J. Biomaterials Appl.*, 6:1, 216–50 (1992).
Bruin et al., "Biodegradable Lysine Diisocyanate–based Poly(glycolide–co–ε–Caprolactone)–Urethane Network in Artificial Skin", *Biomaterials*, 11:4, 291–95 (1990).
Penczek et al., *Handbook of Polymer Synthesis,* Chapter 17: "Phosphorus–Containing Polymers", (Hans R. Kricheldorf ed., 1992).
Sugiyama et al., "Preparation of Poly(phosphate ester)s Having Bisphenol Moieties as Mesogenic Units in the Main Chain," Journal of Polymer Science Part A: Polymer Chemistry Edition 32:11 (1994).
Wu, Xue Shen, "Synthesis and Properties of Biodegradable Lactic/Glycolic Acid Polymers," *Encyclopedic Handbook of Biomaterials and Bioengineering,* vol. 2: 1015 at 1016.
Branham, Keith, "Synthesis and Characterization of Some Organic–Inorganic Polymers," Dissertation, University of Alabama at Birmingham, Abstract, 17–18 (1996).
Lo, Hungnan, "Synthesis of Biodegradable Polymers and Porous Grafts for Orthopedic Application," Thesis, Johns Hopkins University (1995).

* cited by examiner

Primary Examiner—Peter Szekely
(74) Attorney, Agent, or Firm—Foley, Hoag & Eliot LLP

(57) ABSTRACT

Biodegradable, flowable or flexible polymer compositions are described comprising a polymer having the recurring monomeric units shown in formula I:

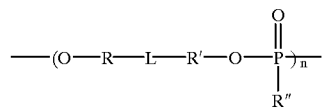

wherein:
  each of R and R' is independently straight or branched alkylene, either unsubstituted or substituted with one or more non-interfering substituents;
  L is a divalent cycloaliphatic group;
  R" is selected from the group consisting of H, alkyl, alkoxy, aryl, aryloxy, heterocyclic or heterocycloxy; and
  n is 5 to 1,000,
wherein said biodegradable polymer is biocompatible before and upon biodegradation. In one embodiment, one or more of R, R' or R" is a biologically active substance. Amorphous compositions containing a biologically active substance, in addition to the polymer, and methods for controllably releasing biologically active substances using the compositions, are also described.

33 Claims, 23 Drawing Sheets

31P-NMR Spectrum

1H-NMR Spectrum

Frequency sweep at 25°C

○ G'
□ G"
● Eta

Temperature dependence of viscosity at 1 Hz

IL-2 release from P(CHDM-HOP) Matrix in RPMI1640 medium containing 10% FCS

—○— ELISA IL-2
—△— Biologically active IL-2

Histology Examination of the Injection Site (s.c.)

BIODEGRADABLE COMPOSITIONS COMPRISING POLY(CYCLOALIPHATIC PHOSPHOESTER) COMPOUNDS, ARTICLES, AND METHODS FOR USING THE SAME

This application is a continuation-in-part application of U.S. patent application Ser. No. 08/841,345, filed Apr. 30, 1997, now abandoned, the contents of which are incorporated herein in their entirety.

BACKGROUND OF THE INVENTION

1. Field of the Invention

The present invention relates to biodegradable poly(phosphoester) compositions that degrade in vivo into non-toxic residues, in particular those containing a cycloaliphatic structure in the polymer backbone. The compositions of the invention are particularly useful as flexible or flowable materials for localized, controlled drug delivery systems.

2. Description of the Prior Art

Biocompatible polymeric materials have been used extensively in therapeutic drug delivery and medical implant applications. If a medical implant is intended for use as a drug delivery or other controlled-release system, using a biodegradable polymeric carrier is one effective means to deliver the therapeutic agent locally and in a controlled fashion, see Langer et al., "Chemical and Physical Structures of Polymers as Carriers for Controlled Release of Bioactive Agents", *J. Macro. Science, Rev. Macro. Chem. Phys.*, C23(1), 61–126 (1983). As a result, less total drug is required, and toxic side effects can be minimized. Polymers have been used for some time as carriers of therapeutic agents to effect a localized and sustained release. See Leong et al., "Polymeric Controlled Drug Delivery", *Advanced Drug Delivery Rev.*, 1:199–233 (1987); Langer, "New Methods of Drug Delivery", *Science*, 249:1527–33 (1990) and Chien et al., *Novel Drug Delivery Systems* (1982). Such delivery systems offer the potential of enhanced therapeutic efficacy and reduced overall toxicity.

When a non-biodegradable polymer matrix is used, the steps leading to release of the therapeutic agent are water diffusion into the matrix, dissolution of the therapeutic agent, and diffusion of the therapeutic agent out through the channels of the matrix. As a consequence, the mean residence time of the therapeutic agent existing in the soluble state is normally longer for a non-biodegradable matrix than for a biodegradable matrix, for which passage through the channels of the matrix, while it may occur, is no longer required.

Since many pharmaceuticals have short half-lives, therapeutic agents can decompose or become inactivated within the non-biodegradable matrix before they are released. This issue is particularly significant for many bio-macromolecules, e.g., proteins and smaller polypeptides, since these molecules are generally hydrolytically unstable and have markedly low permeabilities through most polymer matrices. In nonbiodegradable matrices, many bio-macromolecules even begin to aggregate and precipitate out of solution, blocking the very channels necessary for diffusion out of the carrier matrix.

These problems are alleviated somewhat by using a biodegradable rigid matrix that, in addition to some diffusional release, primarily allows the controlled release of the therapeutic agent by degradation of the solid polymer matrix. Examples of classes of synthetic polymers that have been studied as possible solid biodegradable materials include polyesters (Pitt et al., "Biodegradable Drug Delivery Systems Based on Aliphatic Polyesters: Applications to Contraceptives and Narcotic Antagonists", *Controlled Release of Bioactive Materials*, 19–44 (Richard Baker ed., 1980); poly(amino acids) and pseudo-poly(amino acids) (Pulapura et al. "Trends in the Development of Bioresorbable Polymers for Medical Applications", *J. Biomaterials Appl.*, 6:1, 216–50 (1992); polyurethanes (Bruin et al., "Biodegradable Lysine Diisocyanate-based Poly(Glycolide-co-ε Caprolactone)-Urethane Network in Artificial Skin", *Biomaterials*, 11:4, 291–95 (1990); polyorthoesters (Heller et al., "Release of Norethindrone from Poly(Ortho Esters)", *Polymer Engineering Sci.*, 21:11, 727–31 (1981); and polyanhydrides (Leong et al., "Polyanhydrides for Controlled Release of Bioactive Agents", *Biomaterials* 7:5, 364–71 (1986).

Polymers having phosphate linkages, called poly(phosphates), poly(phosphonates) and poly(phosphites), are known. See Penczek et al., *Handbook of Polymer Synthesis*, Chapter 17: "Phosphorus-Containing Polymers", (Hans R. Kricheldorf ed., 1992). The respective structures of these three classes of compounds, each having a different side chain connected to the phosphorus atom, are as follows:

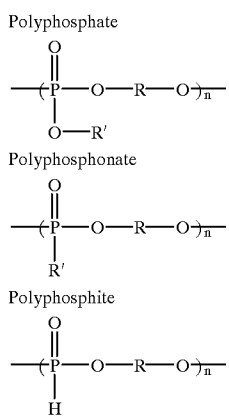

The versatility of these polymers comes from the versatility of the phosphorus atom, which is known for a multiplicity of reactions. Its bonding can involve the 3porbitals or various 3s–3p hybrids; spd hybrids are also possible because of the accessible dorbitals. Thus, the physico-chemical properties of the poly(phosphoesters) can be readily changed by varying either the R or R' group. The biodegradability of the polymer is due primarily to the physiologically labile phosphoester bond in the backbone of the polymer. By manipulating the backbone or the side chain, a wide range of biodegradation rates are attainable.

An additional feature of poly(phosphoesters) is the availability of functional side groups. Because phosphorus can be pentavalent, drug molecules or other biologically active substances can be chemically linked to the polymer. For example, drugs with —O-carboxy groups may be coupled to the phosphorus via a phosphoester bond, which is hydrolyzable. See, Leong, U.S. Pat. Nos. 5,194,581 and 5,256, 765. The P—O—C group in the backbone also lowers the glass transition temperature of the polymer and, importantly, confers solubility in common organic solvents, which is desirable for easy characterization and processing.

However, drug-delivery systems using most of the known biodegradable polymers, including those of phosphoesters, have been rigid materials. In such instances, the drug is incorporated into the polymer, and the mixture is shaped into a certain form, such as a cylinder, disc, or fiber for implantation.

However, proteins and other large biomolecules are still difficult to deliver from rigid biodegradables because these larger molecules are particularly unstable and are typically degraded along with the solid polymeric matrix carrier. More specifically, when a polymer begins to degrade following administration, a highly concentrated microenvironment is created from the breakdown by-products of the polymer as the polymer becomes ionized, protonated or hydrolyzed. Proteins are easily denatured or degraded under these conditions and then are useless for therapeutic purposes.

Further, in the process of preparing rigid drug delivery systems, biologically active substances such as proteins are commonly exposed to extreme stresses. Necessary manufacturing steps may include excessive exposure to heat, pH extremes, large amounts of organic solvents, cross-linking agents, freezing and drying. Following manufacture or preparation, the drug delivery systems must be stored for some extended period of time prior to administration, and little information is available on the subject of long term stability of proteins within solid biodegradable delivery systems.

Rigid polymers can be inserted into the body with a syringe or catheter in the form of small particles, such as microspheres or microcapsules. However, because they are still solid particles, they do not form the continuous and nearly homogeneous, monolithic matrix that is sometimes needed for preferred release profiles.

In addition, microspheres or microcapsules prepared from these polymers and containing biologically active substances to be released into the body are sometimes difficult to produce on a large scale. Most of the microencapsulation processes involve high temperature and contact with organic solvents, steps that tend to damage the bioactivity of proteins. Moreover, their storage often presents problems and, upon injection, their granular nature can cause blockages in injection devices and/or irritation of the soft tissues into which the small particles are injected.

Dunn et al., U.S. Pat. Nos. 5,278,201; 5,278,202; and 5,340,849, disclose a thermoplastic drug delivery system in which a solid, linear-chain, biodegradable polymer or copolymer is dissolved in a solvent to form a liquid solution. Once the polymer solution is placed into the body where there is sufficient water, the solvent dissipates or diffuses away from the polymer leaving it to coagulate or solidify into a solid substance. However, the system requires the presence of a solvent, and it is difficult to find an organic solvent that is sufficiently non-toxic for acceptable biocompatibility.

Thus, there exists a need for a composition and method for providing a flexible or flowable biodegradable composition that can be used in vivo to release a variety of different biologically active substances, including hydrophobic drugs and even large and bulky biomacromolecules, such as therapeutically useful proteins, preferably without requiring the presence of significant amounts of organic solvent. There is also a continuing need for biodegradable polymer compositions that may provide controlled release in such a way that trauma to the surrounding soft tissues can be minimized.

Coover et al., U.S. Pat. No. 3,271,329, discloses organophosphorus polymers prepared from dialkyl or diaryl hydrogen phosphites and certain diol compounds, such as 1,4-cyclohexanedimethanol. See column 1, lines 24–31. Vandenberg et al., U.S. Pat. No. 3,655,585, discloses phosphorous polymers having at least one recurring unit having the formula:

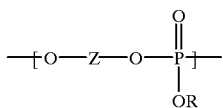

where R can be alkyl and Z can be alkylene such as cyclohexylene. See column 1, lines 28–55. Herwig et al., U.S. Pat. No. 3,875,263, discloses diphosphinic acid esters having a cyclic alkylene portion, e.g., 1,4-methylene-cyclohexane. See column 1, lines 18–37 and column 2, line 13.

However, all of these patents suggest that such compounds and polymeric compositions made from such compounds should be extruded or molded to form articles or spun into fibers (Coover et al.); used as additives for lubricating oils, gasoline, and synthetic resins or other polymers (Vandenberg et al. and Herwig et al.); or used as coating compounds (Herwig et al.). These compounds are known by those of skill in the art primarily as conferring high flame resistance and fire-proofing capabilities (Coover et al. and Herwig et al.) or increased stability to oxidation and heat and improved impact strength (Vandenberg et al.).

SUMMARY OF THE INVENTION

It has now been discovered that polymer compositions made with poly(cycloaliphatic phosphoester) compounds provide conveniently flexible or flowable carriers for even large and/or bulky bio-macromolecules, including hydrophobic drugs and even large and bulky bio-macromolecules, such as therapeutically useful proteins. The biodegradable polymer composition of the invention comprises a polymer having the recurring monomeric units shown in formula I:

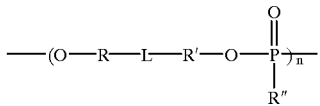

wherein:
each of R and R' is independently straight or branched aliphatic, either unsubstituted or substituted with one or more non-interfering substituents;
L is a divalent cycloaliphatic group;
R" is selected from the group consisting of H, alkyl, alkoxy, aryl, aryloxy, heterocyclic or heterocycloxy; and
n is 5 to 1,000 wherein the biodegradable polymer composition is biocompatible both before and upon biodegradation. In a particularly preferred embodiment, one or more of R, R' and R" is a biologically active substance in a form capable of being released in a physiological environment.

The invention also comprises a flexible article useful for implantation, injection, or otherwise placed totally or partially within the body, the article comprising a biodegradable, flowable or flexible polymer composition comprising a polymer having the recurring monomeric units shown in formula I where R, R', R", L and n are as defined above.

In yet another embodiment of the invention, a method is provided for the controlled release of a biologically active substance comprising the steps of:
(a) combining the biologically active substance with a biodegradable polymer having the recurring monomeric units shown in formula I:

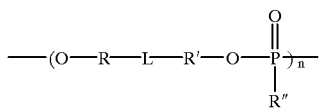

where R, R', L, R" and n are as defined above, to form an implantable or injectable polymer composition; and (b) placing the polymer composition formed in step (a) either partially or totally within the body at a preselected site in vivo, such that the polymer composition is in at least partial contact with a biological fluid.

Because the compositions of the invention are preferably viscous, flowable "gel-like" materials or flexible materials, they can be used to deliver a wide variety of drugs, for example, from hydrophobic drugs such as paclitaxel to large water-soluble macromolecules such as proteins. Even when not flowable, the compositions of the invention are still flexible and allow large proteins to, at least partially, diffuse through the matrix prior to the protein being degraded. The invention thus provides a delivery system that is both convenient for use and capable of delivering large bio-macromolecules in an effective manner.

DETAILED DESCRIPTION OF THE INVENTION

Polymeric Compositions of the Invention

Figure 1A:
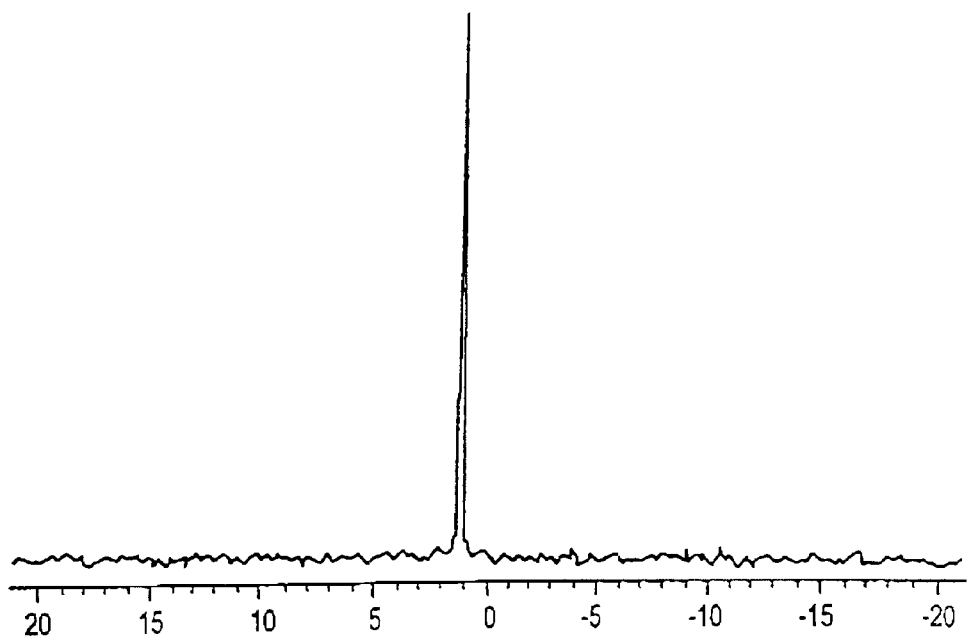
FIG. 1 shows the structure of P(trans-CHDM-HOP) as determined by $^{31}$P-NMR and $^1$H-NMR.

As used herein, the term "aliphatic" refers to a linear, branched or cyclic alkane, alkene, or alkyne. Preferred linear or branched aliphatic groups in the poly(cycloaliphatic phosphoester) composition of the invention have from about 1 to 20 carbon atoms. Preferred cycloaliphatic groups may have one or more sites of unsaturation, i.e., double or triple bonds, but are not aromatic in nature.

As used herein, the term "aryl" refers to an unsaturated cyclic carbon compound with 4n+2 π electrons. As used herein, the term "heterocyclic" refers to a saturated or unsaturated ring compound having one or more atoms other than carbon in the ring, for example, nitrogen, oxygen or sulfur.

As used herein, the term "non-interfering substituent" means a substituent that does react with the monomers; does not catalyze, terminate or otherwise interfere with the polymerization reaction; and does not react with the resulting polymer chain through intra- or inter-molecular reactions.

The biodegradable and injectable polymer composition of the invention comprises a polymer having the recurring monomeric units shown in formula I:

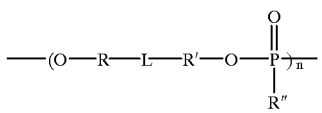

wherein each of R and R' is independently straight or branched aliphatic, either unsubstituted or substituted with one or more non-interfering substituents. Each of R and R' can be any aliphatic moiety so long as the moiety does not interfere undesirably with the polymerization or biodegradation reactions of the polymer.

Preferably, R and R' have from about 1–20 carbon atoms. For example, each of R and R' can be an alkylene group, such as methylene, ethylene, 1,2-dimethylethylene, n-propylene, isopropylene, 2-methylpropylene, 2,2-dimethylpropylene or tert-butylene, n-pentylene, tert-pentylene, n-hexylene, n-heptylene and the like; alkenylene, such as ethenylene, propenylene, dodecenylene, and the like; alkynylene, such as propynylene, hexynylene, octadecenynylene, and the like; an aliphatic group substituted with a non-interfering substituent, for example, hydroxy-, halogen- or nitrogen-substituted aliphatic group. Preferably, however, each of R and R' is a branched or straight chain alkylene group and, even more preferably, an alkylene group having from 1 to 7 carbon atoms. Most preferably, R is a methylene or ethylene group.

In one embodiment of the invention, either R, R', or both R and R', can be a biologically active substance in a form capable of being released in a physiological environment. When the biologically active substance is part of the poly (phosphoester) backbone in this way, it is released as the polymeric matrix formed by the composition of the invention degrades.

Generally speaking, the biologically active substance of the invention can vary widely with the purpose for the composition. The term "biologically active substance" includes without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a predetermined physiological environment. The active substance(s) may be described as a single entity or a combination of entities.

Non-limiting examples of broad categories of biologically active substances include the following expanded therapeutic categories: β-adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheals, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, humoral agents, hyperglycemic agents, hypnotics, hypoglycemic agents, ion exchange resins, laxatives, mineral supplements, miotics, imucolytic agents, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and pro-drugs.

Specific examples of useful biologically active substances from the above categories include: (a) anti-neoplastics such as androgen inhibitors, antimetabolites, cytotoxic agents, and immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate, and morphine; (f) mineral supplements such as potassium chloride, zinc chloride, calcium carbonate, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (m) desensitizing agents and antigenic materials, such as those useful for vaccine applications.

More specifically, non-limiting examples of useful biologically active substances include the following therapeutic categories: analgesics, such as nonsteroidal anti-inflammatory drugs, opiate agonists and salicylates; antihistamines, such as $H_1$-blockers and $H_2$-blockers; anti-infective agents, such as antihelmintics, antianaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, β-blocker sympatholytics, sympathomimetics, and adrenergic agonist sympathomimetics; cardiovascular agents, such as antianginals, β-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, α-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and pro-kinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, antiandrogens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, antiparkinsonian agents, anti-vertigo agents, opiate agonists, and opiate antagonists; ophthalmic agents, such as anti-glaucoma agents, β-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Preferred classes of useful biologically active substances from the above categories include: (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) $H_2$-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous β-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) anti-protozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) α-blocker sympatholytics, such as prazosin; (34) β-blocker sympatholytics, such as atenolol; (35) adrenergic agonist sympathomimetics, such as albuterol and dobutamine; (36) cardiovascular agents, such as aspirin (ASA) (enteric coated ASA); (37) β-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenytoin, procainamide, and quinidine; (42) class II antiarrhythmics, such as atenolol, metoprolol, propranolol, and timolol; (43)

class III antiarrhythmics, such as amiodarone; (44) class IV antiarrhythmics, such as diltiazem and verapamil; (45) α-blocker antihypertensives, such as prazosin; (46) angiotensin-converting enzyme inhibitor (ACE inhibitor) antihypertensives, such as captopril and enalapril; (47) β-blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) H$_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic anti-anemia agents, such as erythropoietin, filgrastim (G-CSF), and sargramostim (GM-CSF); (78) coagulation agents, such as antihemophilic factors 1–10 (AHF 1–10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-lb and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkinsonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) β-blocker anti-glaucoma agents, such as timolol; (110) miotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B$_{12}$) and niacin (vitamin B$_3$); (128) vitamin C compounds, such as ascorbic acid; and (129) vitamin D compounds, such as calcitriol.

In addition to the foregoing, the following less common drugs may also be used: chlorhexidine; estradiol cypionate in oil; estradiol valerate in oil; flurbiprofen; flurbiprofen sodium; ivermectin; levodopa; nafarelin; and somatropin.

Further, the following new drugs may also be used: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan.

Further still, the following intravenous products may be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alfa; leuprolide acetate; meperidine HCl; methadone HCl; methotrexate sodium; paclitaxel; ranitidine HCl; vinblastin sulfate; and zidovudine (AZT).

Still further, the following listing of peptides, proteins, and other large molecules may also be used, such as interleukins 1 through 18, including mutants and analogues; interferons α, β, and γ; luteinizing hormone releasing hormone (LHRH) and analogues, gonadatropin releasing hormone (GnRH), transforming growth factor-β (TGF-β); fibroblast growth factor (FGF); tumor necrosis factor-α & β (TNF-α & β); nerve growth factor (NGF); growth hormone releasing factor (GHRF); epidermal growth factor (EGF); fibroblast growth factor homologous factor (FGFHF); hepatocyte growth factor (HGF); insulin growth factor (IGF); platelet-derived growth factor (PDGF); invasion inhibiting factor-2 (IIF-2); bone morphogenetic proteins 1–7 (BMP 1–7); somatostatin; thymosin-α-1; γ-globulin; superoxide dismutase (SOD); and complement factors.

Alternatively, the biologically active substance may be nucleic acids comprised of nucleotides linked together into polynucleotide chains with backbones consisting of alternating series of pentose sugars and phosphate residues. One way to avoid the complications of developing cell-based systems for delivering genes to patients in gene therapy is to deliver retroviral vectors directly to target cells. For example, this technique has been used to infect endothelial cells of blood vessel walls. The polymers and compositions of the invention may be used for direct delivery of such retroviral vectors and/or related genetic materials to other sites in vivo, for example, to the lungs to treat ailments in the lungs, such as cystic fibrosis, or to treat tumors in any localized portion of the body.

Preferably, the biologically active substance is selected from the group consisting of peptides, polypeptides, proteins, amino acids, polysaccharides, growth factors, hormones, anti-angiogenesis factors, interferons or cytokines, antigenic materials, and pro-drugs. In a particularly preferred embodiment, the biologically active substance is a therapeutic drug or pro-drug, most preferably a drug selected from the group consisting of chemotherapeutic agents and other anti-neoplastics such as paclitaxel, antibiotics, anti-virals, anti-fungals, anti-inflammatories, and anticoagulants, antigens useful for vaccine applications or corresponding pro-drugs.

Various forms of the biologically active agents may be used. These include, without limitation, such forms as uncharged molecules, molecular complexes, salts, ethers, esters, amides, and the like, which are biologically activated when implanted, injected or otherwise placed into the body.

L in the polymer composition of the invention can be any divalent cycloaliphatic group so long as it does not interfere with the polymerization or biodegradation reactions of the polymer of the composition. Specific examples of useful L groups include unsubstituted and substituted cycloalkylene groups, such as cyclopentylene, 2-methyl-cyclopentylene, cyclohexylene, 2-chlorocyclohexylene, and the like; cycloalkenylene groups, such as cyclohexenylene; and cycloalkylene groups having fused or bridged additional ring structures on one or more sides, such as tetralinylene, decalinylene, and norpinanylene; or the like.

R" in the polymer composition of the invention is an alkyl, alkoxy, aryl, aryloxy, heterocyclic or heterocycloxy residue. Examples of useful alkyl R" groups include methyl, ethyl, n-propyl, i-propyl, n-butyl, tert-butyl, —$C_8H_{17}$, and the like groups; alkyl substituted with a non-interfering substituent, such as a halogen group; corresponding alkoxy groups; and alkyl that is conjugated with a biologically active substance to form a pendant drug delivery system.

When R" is alkyl or alkoxy, it preferably contains about 2 to about 20 carbon atoms, even more preferably about 6 to about 15 carbon atoms. When R" is aryl or the corresponding aryloxy group, it typically contains from about 5 to about 14 carbon atoms, preferably about 5 to 12 carbon atoms and, optionally, can contain one or more rings that are fused to each other. Examples of particularly suitable aromatic groups include phenyl, phenoxy, naphthyl, anthracenyl, phenanthrenyl and the like.

When R" is heterocyclic or heterocycloxy, it typically contains from about 5 to 14 ring atoms, preferably from about 5 to 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin-, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthpyridine, pyrido[3,4-b]-pyridine, pyrido[3,2-b]-pyridine, pyrido[4,3-b]pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. Preferably, when R" is heterocyclic or heterocycloxy, it is selected from the group consisting of furan, pyridine, N-alkylpyridine, 1,2,3- and 1,2,4-triazoles, indene, anthracene and purine rings.

In a particularly preferred embodiment, R" is an alkyl group, an alkoxy group, a phenyl group, a phenoxy group, or a heterocycloxy group and, even more preferably, an alkoxy group having from 1 to 10 carbon atoms. Most preferably, R" is an ethoxy or hexyloxy group.

Alternatively, the side chain R" can be a biologically active substance pendently attached to the polymer backbone, for example by ionic or covalent bonding. In this pendant system, the biologically active substance is released as the bond connecting R" with the phosphorous atom is cleaved under physiological conditions.

The number "n" can vary greatly depending on the biodegradability and the release characteristics desired in the polymer, but typically varies between about 5 and 1,000. Preferably, n is from about 5 to about 500 and, most preferably, from about 5 to about 200.

The molecular weight of the polymer used in the composition of the invention can vary widely, but must remain low enough for the polymer to maintain its flowable or flexible state. For example, weight-average molecular weights (Mw) typically vary from about 2,000 to about 400,000 daltons, preferably from about 2,000 to about 200,000 daltons and, most preferably, from about 2,000 to 50,000 daltons. Number-average molecular weight (Mn) can also vary widely, but generally fall in the range of about 1,000 to about 200,000 daltons, preferably from about 1,000 to about 100,000 daltons and, most preferably, from about 1,000 to about 25,000 daltons.

Biodegradable polymers differ from non-biodegradable polymers in that they can be degraded during in vivo therapy. This generally involves breaking down the polymer into its monomeric subunits. In principle, the ultimate hydrolytic breakdown products of the polymer used in the invention are a cycloaliphatic diol, an aliphatic alcohol and phosphate. All of these degradation products are potentially non-toxic. However, the intermediate oligomeric products of the hydrolysis may have different properties. Thus, the toxicology of a biodegradable polymer intended for injection or placing totally or partially within the body, even one synthesized from apparently innocuous monomeric structures, is typically determined after one or more toxicity analyses.

There are many different ways of testing for toxicity and/or biocompatibility known to those of ordinary skill in the art. A typical in vitro toxicity assay, however, would be performed with live carcinoma cells, such as GT3TKB tumor cells, in the following manner:

Two hundred microliters of various concentrations of the degraded polymer products are placed in 96-well tissue culture plates seeded with human gastric carcinoma cells (GT3TKB) at $10^4$/well density. The degraded polymer products are incubated with the GT3TKB cells for 48 hours. The results of the assay can be plotted as % relative growth vs. concentration of degraded polymer in the tissue-culture well.

Polymers for use in medical applications, such as drug delivery systems, can also be evaluated by well-known in vivo biocompatibility tests, such as by subcutaneous implantation or injection in rats to confirm that the systems hydrolyze without significant levels of irritation or inflammation at the insertion site.

The biodegradable polymer used in the invention is preferably sufficiently pure to be biocompatible itself and remains biocompatible upon biodegradation. By "biocompatible", it is meant that the biodegradation products or the polymer itself are non-toxic and result in only minimal tissue irritation when injected or placed into intimate contact with vasculated tissues. The requirement for biocompatibility is more easily accomplished because the presence of an organic solvent is not required in the polymer composition of the invention.

However, the polymer used in the invention is preferably soluble in one or more common organic solvents for ease of synthesis, purification and handling. Common organic solvents include such solvents as ethanol, chloroform, dichloromethane, acetone, ethyl acetate, DMAC, N-methyl pyrrolidone, dimethylformamide, and dimethylsulfoxide. The polymer is preferably soluble in at least one of the above solvents.

The polymer of the invention can also comprise additional biocompatible monomeric units so long as they do not interfere with the biodegradable characteristics and the desirable flow characteristics of the invention. Such additional monomeric units may offer even greater flexibility in designing the precise release profile desired for targeted drug delivery or the precise rate of biodegradability desired for other applications. When such additional monomeric units are used, however, they should be used in small enough amounts to insure the production of a biodegradable copolymer having the desired physical characteristics, such as viscosity, flowability, flexibility or morphology.

Examples of such additional biocompatible monomers include the recurring units found in other poly (phosphoesters), poly(lactides), poly(glycolides), poly (caprolactones), poly[]anhydrides)J poly(amides), poly (urethanes), poly(esteramides), poly(orthoesters), poly (dioxanones), poly(acetals), poly(ketals), poly(carbonates), poly(orthocarbonates), poly(phosphazenes), poly (hydroxybutyrates), poly(hydroxyvalerates), poly(alkylene oxalates), poly(alkylene succinates), poly(malic acids), poly (amino acids), poly(vinylpyrrolidone), poly(ethylene glycol), poly(hydroxycellulose), chitin, chitosan, and copolymers, terpolymers, or combinations or mixtures of the above materials.

When additional monomeric units are used, those which have a lower degree of crystallization and are more hydrophobic are preferred. Especially preferred recurring units with the desired physical characteristics are those derived from poly(lactides), poly(caprolactones), and copolymers of these with glycolide, in which there are more amorphous regions.

Synthesis of Poly(cycloaliphatic phosphoester) Polymers

The most common general reaction in preparing poly(phosphates) is a dehydrochlorination between a phosphorodichloridate and a diol according to the following equation:

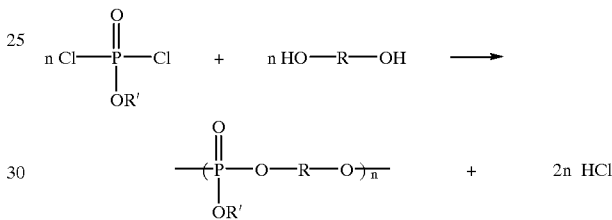

Most poly(phosphonates) are also obtained by condensation between appropriately substituted dichlorides and diols.

Poly(phosphites) have been prepared from glycols in a two-step condensation reaction. A 20% molar excess of a dimethylphosphite is used to react with the glycol, followed by the removal of the methoxyphosphonyl end groups in the oligomers by high temperature.

An advantage of melt polycondensation is that it avoids the use of solvents and large amounts of other additives, thus making purification more straightforward. It can also provide polymers of reasonably high molecular weight. Somewhat rigorous conditions, however, are often required and can lead to chain acidolysis (or hydrolysis if water is present). Unwanted, thermally-induced side reactions, such as crosslinking reactions, can also occur if the polymer backbone is susceptible to hydrogen atom abstraction or oxidation with subsequent macroradical recombination.

To minimize these side reactions, the polymerization can also be carried out in solution. Solution polycondensation requires that both the prepolymer and the phosphorus component be soluble in a common solvent. Typically, a chlorinated organic solvent is used, such as chloroform, dichloromethane, or dichloroethane.

The solution polymerization is preferably run in the presence of equimolar amounts of the reactants and a stoichiometric amount of an acid acceptor, usually a tertiary amine such as pyridine or triethylamine. The product is then typically isolated from the solution by precipitation in a non-solvent and purified to remove the hydrochloride salt by conventional techniques known to those of ordinary skill in the art, such as by washing with an aqueous acidic solution, e.g., dilute HCl.

Reaction times tend to be longer with solution polymerization than with melt polymerization. However, because overall milder reaction conditions can be used, side reactions are minimized, and more sensitive functional groups can be incorporated into the polymer. Moreover, attainment of undesirably high molecular weights is less likely with solution polymerization.

Interfacial polycondensation can be used when high reaction rates are desired. The mild conditions used minimize side reactions, and there is no need for stoichiometric equivalence between the diol and dichloridate starting materials as in solution methods. However, hydrolysis of the acid chloride may occur in the alkaline aqueous phase. Sensitive dichloridates that have some solubility in water are generally subject to hydrolysis rather than polymerization. Phase transfer catalysts, such as crown ethers or tertiary ammonium chloride, can be used to bring the ionized diol to the interface to facilitate the polycondensation reaction. The yield and molecular weight of the resulting polymer after interfacial polycondensation are affected by reaction time, molar ratio of the monomers, volume ratio of the immiscible solvents, the type of acid acceptor, and the type and concentration of the phase transfer catalyst.

In a preferred embodiment of the invention, the biodegradable polymer of formula I is made by a process comprising the step of reacting a diol having the formula:

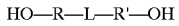

wherein R, R' and L are as defined above, with a phosphorodihalidate of formula II:

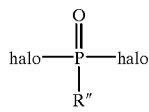

where "halo" is Br, Cl or I, and R– is as defined above, to form the polymer of formula I. The diol HO—R—L—R'—OH can be prepared by standard procedures of chemistry, and many such compounds are available on a commercial basis.

When either R or R' is a biologically active substance, the biologically active substance is preferably itself a diol, for example, a steroid such as estradiol. Alternatively, the biologically active substance can be a diamino compound that is reacted with the carboxyl group of a carboxylic acid to produce terminal hydroxyl groups that can be used to form the poly(phosphoester) structure.

The purpose of the polymerization reaction is to form a polymer comprising (i) cycloaliphatic recurring units and (ii) phosphoester recurring units. The result can be a homopolymer, a relatively homogeneous copolymer, or a block copolymer that has a somewhat heterogeneous microcrystalline structure. Any one of these three embodiments is well-suited for use as a controlled release medium.

The process used to make the polymers used in the invention can take place at widely varying temperatures, depending upon whether a solvent is used and, if so, which one; the molecular weight desired; the solubility desired; the susceptibility of the reactants to form side reactions; and the presence of a catalyst. Preferably, however, the process takes place at a temperature ranging from about 0 to about +235° C. for melt conditions. Somewhat lower temperatures, e.g., from about –50 to about 100° C., may be possible with solution polymerization or with the use of either a cationic or anionic catalyst.

The time required for the process can also vary widely, depending upon the type of reaction being used, the molecular weight desired and, in general, the need to use more or less rigorous conditions for the reaction to proceed to the desired degree of completion. Typically, however, the process takes place during a time between about 30 minutes and 4 days.

While the process may be in bulk, in solution, by interfacial polycondensation, or any other convenient method of polymerization, preferably, the process takes place under solution conditions. Particularly useful solvents include methylene chloride, chloroform, tetrahydrofuran, dimethyl formamide, dimethyl sulfoxide, toluene, or any of a wide variety of other inert organic solvents.

Particularly when solution polymerization reaction is used, an acid acceptor is advantageously present during the polymerization reaction. A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

The addition sequence for solution polymerization can vary significantly depending upon the relative reactivities of the diol; the phosphorodihalidate of formula II; the purity of these reactants; the temperature at which the polymerization reaction is preformed; the degree of agitation used in the polymerization reaction; and the like. Preferably, however, the diol is combined with a solvent and an acid acceptor, and then the phosphorodihalidate is added slowly. For example, a solution of the phosphorodihalidate in a solvent may be trickled in or added dropwise to the chilled reaction mixture of diol, solvent and acid acceptor, to control the rate of the polymerization reaction.

The polymer of formula I is isolated from the reaction mixture by conventional techniques, such as by precipitating out, extraction with an immiscible solvent, evaporation, filtration, crystallization and the like. Typically, however, the polymer of formula I is both isolated and purified by quenching a solution of the polymer with a non-solvent or a partial solvent, such as diethyl ether or petroleum ether.

Biodegradability and Release Characteristics

The polymer of formula I is usually characterized by a biodegradation rate that is controlled at least in part as a function of hydrolysis of the phosphoester bond of the polymer. Other factors are also important. For example, the lifetime of a biodegradable polymer in vivo also depends upon its molecular weight, crystallinity, biostability, and the degree of crosslinking. In general, the greater the molecular weight, the higher the degree of crystallinity, and the greater the biostability, the slower biodegradation will be. In addition, the rate of degradation of the polymer can be further controlled by choosing a side chain of differing lengths. Accordingly, degradation times can very widely, preferably from less than a day to several months.

Accordingly, the structure of the side chain can influence the release behavior of compositions comprising a biologically active substance. For example, it is expected that conversion of the phosphate side chain to a more lipophilic, more hydrophobic or bulky group would slow down the degradation process. Thus, release is usually faster from polymer compositions with a small aliphatic group side chain than with a bulky aromatic side chain. Moreover, when R and/or R' in the backbone portion of formula I is itself a biologically active substance, the release rate of the biologically active substance in vivo is primarily governed by the rate of biodegradation. When the biologically active substance to be released is conjugated to the phosphorus side chain R" to form a pendant drug delivery system, the release profile is governed to a significant degree by the lability of the phosphorous-R" bond.

The mechanical properties of the polymer are also important with respect to the flowability or flexibility of the composition containing the polymer. For example, the glass transition temperature is preferably low enough to keep the composition of the invention flowable at body temperature. Even more preferably, the glass transition temperature of the polymer used in the invention is about 0 to about 37° C. and, most preferably, from about 0 to about 25° C.

Polymer Compositions

The polymer composition of the invention may be a flexible or flowable material. By "flowable" is meant the ability to assume, over time, the shape of the space containing it at body temperature. This includes, for example, liquid compositions that are capable of being sprayed into a site; injected with a manually operated syringe fitted with, for example, a 23-gauge needle; or delivered through a catheter.

Also included by the term "flowable", however, are highly viscous, "gel-like" materials at room temperature that may be delivered to the desired site by pouring, squeezing from a tube, or being injected with any one of the commercially available power injection devices that provide injection pressures greater than would be exerted by manual means alone for highly viscous, but still flowable, materials. When the polymer used is itself flowable, the polymer composition of the invention, even when viscous, need not include a biocompatible solvent to be flowable, although trace or residual amounts of biocompatible solvents may still be present. The viscosity of the polymer can be adjusted by the molecular weight of the polymer, as well as by mixing the cis- and trans- isomers of the cyclohexane dimethanol in the backbone of the polymer.

Even without the presence of a biologically active substance, the polymer composition of the invention can be used for a variety of medical applications. For example, it can be injected to form, after injection, a temporary biomechanical barrier to coat or encapsulate internal organs or tissues, such as the barriers used to prevent adhesions after abdominal surgery. The polymer composition of the invention can also be used to produce bone waxes and fillers for repairing injuries to bone or connective tissue, temporary internal "bandages" to prevent further internal injury or promote internal wound healing, or coatings for solid implantable devices.

The biodegradable composition can even be injected subdermally to build up tissue or to fill in defects. The injected polymer composition will slowly biodegrade within the body and allow natural tissue to grow and replace the polymer matrix as it disappears. Thus, when the material is injected into a soft-tissue defect, it will fill that defect and provide a scaffold for natural collagen tissue to grow. This collagen tissue will gradually replace the biodegradable polymer. However, preferably, the polymer composition of the invention does comprise a biologically active substance and provides controllable and effective release of the biologically active substance over time, even in the case of large bio-macromolecules. Thus, in a preferred embodiment, the biodegradable polymer composition comprises both:

(a) at least one biologically active substance and
(b) the polymer having the recurring monomeric units shown in formula I where R, R' , L, R" and n are as defined above.

The biologically active substances are used in amounts that are therapeutically effective, which varies widely depending largely on the particular biologically active substance being used. The amount of biologically active substance incorporated into the composition also depends upon the desired release profile, the concentration of the substance required for a biological effect, and the length of time that the biologically active substance has to be released for treatment. Preferably, the biologically active substance can be easily blended with the polymer matrix of the invention at different loading levels, at room temperature and without the need for an organic solvent. However, it is also possible to use a solvent during the blending process for more rapid or complete blending, and then evaporate off the solvent when blending is complete.

There is no critical upper limit on the amount of biologically active substance incorporated except for that of an acceptable solution or dispersion viscosity to maintain the physical characteristics desired for the composition. The lower limit of the substance incorporated into the delivery system is dependent upon the activity of the drug and the length of time needed for treatment. Thus, the amount of the biologically active substance should not be so small that it fails to produce the desired physiological effect, nor so large that the biologically active substance is released in an uncontrollable manner.

Typically, within these limits, amounts of the biologically active substance from about 1% up to about 65% can be incorporated into the present delivery systems. However, lesser amounts may be used to achieve efficacious levels of treatment for biologically active substances that are particularly potent.

In addition, the polymer composition of the invention can also comprise blends of the polymer of the invention with other biocompatible polymers or copolymers, so long as the additional polymers or copolymers do not interfere undesirably with the biodegradable or mechanical characteristics of the composition. Blends of the polymer of the invention with such other polymers may offer even greater flexibility in designing the precise release profile desired for targeted drug delivery or the precise rate of biodegradability desired. Examples of such additional biocompatible polymers include other poly(phosphoesters), poly(carbonates), polytesters), poly(orthoesters), poly(phosphazenes), poly (amides), poly(urethanes), poly(imino-carbonates), and poly (anhydrides).

Pharmaceutically acceptable polymeric carriers may also comprise a wide range of additional materials. Without being limited thereto, such materials may include diluents, binders and adhesives, lubricants, disintegrants, colorants, bulking agents, flavorings, sweeteners, and miscellaneous materials such as buffers and adsorbents, in order to prepare a particular medicated composition, with the condition that none of these additional materials will interfere with the biocompatibility, biodegradability and flowability or flexibility of the polymer compositions of the invention.

For delivery of a biologically active substance, the biologically active substance is added to the polymer composition. The biologically active substance is either dissolved to form a homogeneous solution of reasonably constant concentration in the polymer composition, or dispersed to form a suspension or dispersion within the polymer composition at a desired level of "loading" (grams of biologically active substance per grams of total composition including the biologically active substance, usually expressed as a percentage).

While it is possible that the biodegradable polymer or the biologically active agent may be dissolved in a small quantity of a solvent that is non-toxic to more efficiently produce a homogeneous, monolithic distribution or a fine dispersion of the biologically active agent in the flexible or flowable composition, it is an advantage of the invention that, in a preferred embodiment, no solvent is needed to form a flowable composition. Moreover, the use of solvents is preferably avoided because, once a polymer composition containing solvent is placed totally or partially within the body, the solvent dissipates or diffuses away from the polymer and must be processed and eliminated by the body, placing an extra burden on the body's clearance ability at a time when illness or injury may have already deleteriously affected it.

However, when a solvent is used to facilitate mixing or to maintain the flowability of the polymer composition of the invention, it should be non-toxic, otherwise biocompatible, and should be used in minimal amounts. Solvents that are toxic clearly should not be used in any material to be placed even partially within a living body. Such a solvent also must not cause tissue irritation or necrosis at the site of administration.

Examples of suitable biocompatible solvents, when used, include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, dimethylsulfoxide, oleic acid, or 1-dodecylazacycloheptan-2-one. Preferred solvents include N-methyl-2-pyrrolidone, 2-pyrrolidone, dimethyl sulfoxide, and acetone because of their solvating ability and their biocompatibility.

Flowable or Flexible Delivery Systems

In its simplest form, a biodegradable therapeutic agent delivery system consists of a solution or dispersion of a biologically active substance in a polymer matrix having an unstable (biodegradable) bond incorporated into the polymer backbone. Cleavage of the bond converts a water-insoluble polymer into water-soluble, low molecular weight polymer fragments that can be excreted from the body.

The biologically active substance is typically released from the polymeric matrix at least as quickly as the matrix biodegrades in vivo. With some biologically active substances, the substance will be released only after the polymer has been degraded to a point where a non-diffusing substance has been exposed to bodily fluids. As the polymer begins to degrade, the biologically active substance that was completely surrounded by the polymer matrix begins to be liberated. However, with this mechanism, a long peptide chain that is physically entangled in a rigid solid implant structure may tend to degrade along with the matrix and break off from the remainder of the peptide chain, thereby releasing incomplete fragments of molecules.

With the polymer compositions of the invention, however, the polymer will typically degrade after the peptide or protein has been released in part. In a particularly preferred mechanism, when a peptide chain is being released from the composition of the invention, the composition remains flexible and allows a large-molecule protein to, at least partially, diffuse through the polymeric matrix prior to its own or the polymer's biodegradation.

The initial release rate of proteins from the compositions is therefore generally diffusion-controlled through channels in the matrix structure, the rate of which is inversely proportional to the molecular weight of the protein. Once polymer degradation begins, however, the protein remaining in the matrix may also be released by the forces of erosion.

The biodegradable amorphous matrices of the invention typically contain polymer chains that are associated with other chains. These associations can be created by a simple entanglement of polymer chains within the matrix, as opposed to hydrogen bonding or Van der Vaals interactions or between crystalline regions of the polymer or interactions that are ionic in nature. Alternatively, the synthesis of block copolymers or the blending of two different polymers can be used to create viscous, "putty-like" materials with a wide variation in physical and mechanical properties.

When the biologically active substance is a protein, interactions between specific proteins and the polymeric materials often also affect the characteristics of the composition. Important factors include:

(i) the molecular weight of the protein, which is an important parameter with regard to diffusion characteristics;

(ii) the isoelectric point of the protein, which governs charge-charge interactions;

(iii) the presence of cysteines on the protein, which may participate in the formation of intermolecular disulfide bonds;

(iv) the primary amino acid sequence of the protein, which may be susceptible to chemical modification in association with a polymeric material;

(v) the presence or absence of carbohydrates on the protein, which may enhance or prevent interaction with polymeric materials;

(vi) the relative hydrophobicity of a protein, which can interact with hydrophobic sites on a polymer; and (vii) the heterogeneity of the protein, which often exists when proteins are produced by recombinant methods.

In a particularly preferred embodiment, the composition of the invention is sufficiently flowable to be injected into the body. It is particularly important that the injected composition result in minimal tissue irritation after injection or otherwise being placed into direct contact with vasculated tissues.

The biologically active substance of the composition and the polymer of the invention may form a homogeneous matrix, or the biologically active substance may be encapsulated in some way within the polymer. For example, the biologically active substance may be first encapsulated in a microsphere and then combined with the polymer in such a way that at least a portion of the microsphere structure is maintained. Alternatively, the biologically active substance may be sufficiently immiscible in the polymer of the invention that it is dispersed as small droplets, rather than being dissolved, in the polymer. Either form is acceptable, but it is preferred that, regardless of the homogeneity of the composition, a significant portion of the biologically active substance is released in vivo prior to the biodegradation of the polymer by hydrolysis of the phosphoester bond.

In one embodiment, the polymer composition of the invention is used to form a soft, drug-delivery "depot" that can be administered as a liquid, for example, by injection, but which remains sufficiently viscous to maintain the drug within the localized area around the injection site. The degradation time of the depot so formed can be varied from several days to a few years, depending upon the polymer selected and its molecular weight. By using a polymer composition in flowable form, even the need to make an incision can be eliminated. In any event, the flexible or flowable delivery "depot" will adjust to the shape of the space it occupies within the body with a minimum of trauma to surrounding tissues.

The flexible or flowable polymer composition of the invention can be placed anywhere within the body, including soft tissue such as muscle or fat; hard tissue such as bone or cartilage; a cavity such as the periodontal, oral, vaginal, rectal or nasal cavity; or a pocket such as a periodontal pocket or the cul-de-sac of the eye. The composition may also be sprayed onto or poured into open wounds or used as a site delivery system during surgery.

When flowable, the composition of the invention can be injected into deeper wounds, such as burn wounds, to prevent the formation of deep scars. The composition can also be used to act as a temporary barrier in preventing the direct adhesion of different types of tissue to each other, for example, after abdominal surgery, due to its ability to encapsulate tissues, organs and prosthetic devices.

In gene therapy, the flexible or flowable composition of the invention may be useful for providing a means for delivering genes to patients without involving a cell-based system. In particular, the composition of the invention may be injected into sites that would otherwise be inaccessible for direct delivery of gene vectors. In addition, depending upon the need for continued gene therapy, the sustained release capability of the biologically active substance from the composition of the invention would eliminate the need for repeated invasive procedures to re-introduce the gene vector to the involved site.

In orthopedic applications, the flowable or flexible composition of the invention may be useful for repairing bone defects and connective tissue injuries. For example, the biodegradable composition can be loaded with bone morphogenetic proteins to form a bone graft useful for even large segmental defects, when the bone can be immobilized and supported. The composition can also be injected into an appropriate orthopedic space to facilitate cell adhesion and proliferation before the polymeric matrix degrades to non-toxic residues.

Once injected, the polymer composition of the invention should remain in at least partial contact with a biological fluid, such as blood, internal organ secretions, mucous membranes, cerebrospinal fluid and the like. For drug-delivery systems, the implanted or injected composition will release the biologically active substance contained within its matrix at a controlled rate until the substance is depleted, following the general rules for diffusion or dissolution of a biologically active substance from a biodegradable polymeric matrix.

The following examples are illustrative of preferred embodiments of the invention and are not to be construed as limiting the invention thereto. All polymer molecular weights are average molecular weights. All percentages are based on the percent by weight of the final delivery system or formulation being prepared, unless otherwise indicated, and all totals equal 100% by weight.

EXAMPLES

Example 1
Synthesis of the Poly(phosphoester) P(trans-CHDM-HOP)

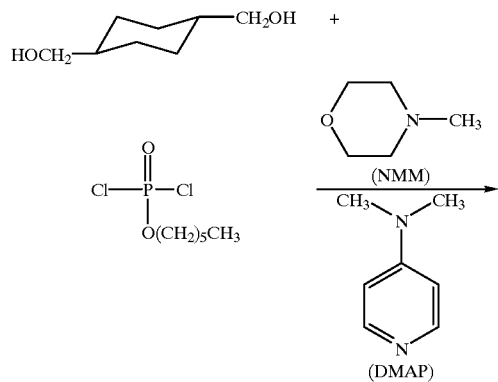

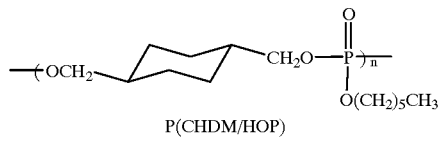

P(CHDM/HOP)

Under an argon stream, 10 g of trans-1,4-cyclohexane dimethanol (CHDM), 1.794 g of 4-dimethylaminopyridine (DMAP), 15.25 ml (14.03 g) of N-methyl morpholine (NMM), and 50 ml of methylene chloride, were transferred into a 250 ml flask equipped with a funnel. The solution in the flask was cooled down to −15° C. with stirring, and a solution of 15.19 g of hexyl phosphorodichloridate (HOP) in 30 ml of methylene chloride was added through the funnel. The temperature of the reaction mixture was raised to the boiling point gradually and maintained at reflux temperature overnight.

Figure 1B:
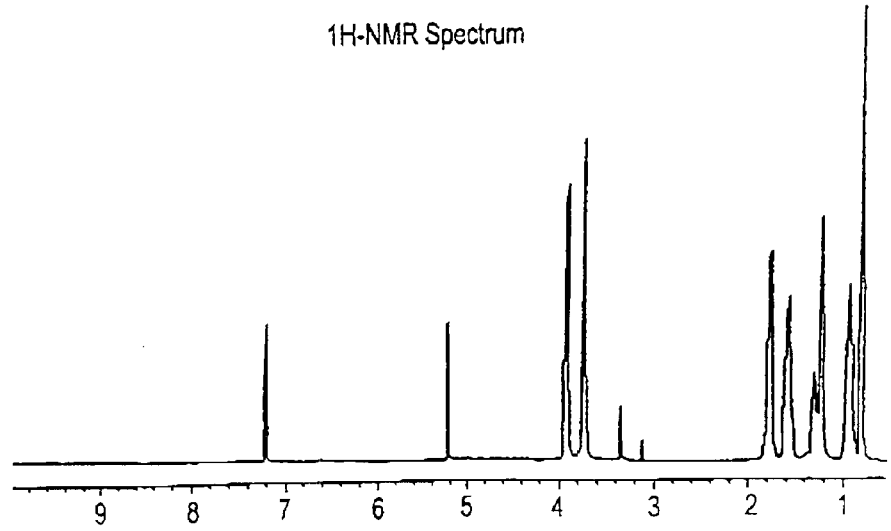
Figure 2A:
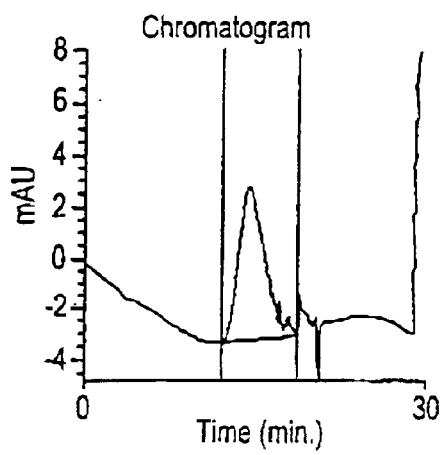
FIG. 2 shows the chromatogram and molecular weight distribution for P(cis-/trans-CHDM-HOP).
Figure 2B:
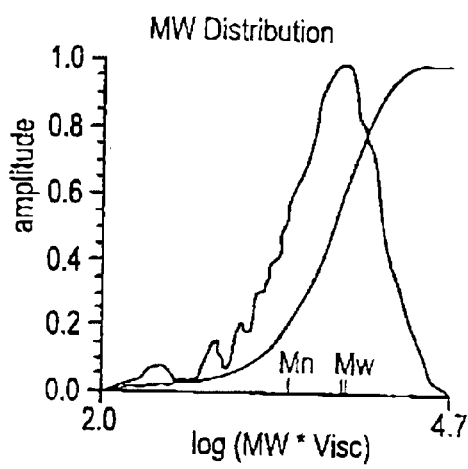
Figure 2C:
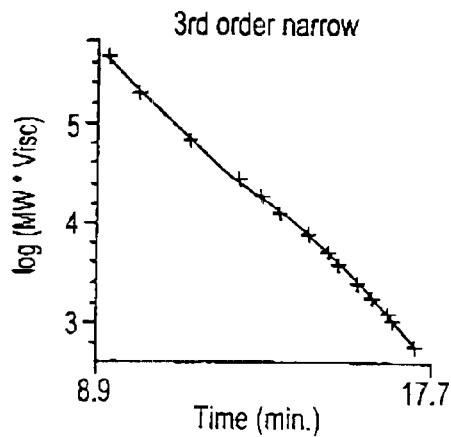

The reaction mixture was filtered, and the filtrate was evaporated to dryness. The residue was re-dissolved in 100 ml of chloroform. This solution was washed with 0.1 M solution of a mixture of HCl and NaCl, dried over anhydrous $Na_2SO_4$, and quenched into 500 ml of ether. The resulting flowable precipitate was collected and dried under vacuum to form a clear pale yellow gel-like polymer with the flow characteristics of a viscous syrup. The yield for this polymer was 70–80%. The structure of P(trans-CHDM-HOP) was ascertained by $^{31}$P-NMR and $^1$H-NMR spectra, as shown in FIG. 1, and by FT-IR spectra. The molecular weights (Mw=8584; Mn=3076) were determined by gel permeation chromatography (GPC), as shown in FIG. 2, using polystyrene as a calibration standard.

Example 2
Synthesis of the Poly(Phosphoester) P(cis & trans-CHDM-HOP)

Poly(phosphoester) P(cis/trans-11,4-cyclohexane-dimethanol hexyl phosphate) was prepared by following the procedure described above in Example 1 except that a mixture of cis- and trans-1,4-cyclohexanedimethanol was used as the starting material. As expected, the product cis-/trans-P(CHDM-HOP) was less viscous than the transisomer obtained in Example 1.

Example 3
Synthesis of Low Molecular Weight P(CHDM-HOP)

Under an argon stream, 10 g of trans-1,4-cyclohexane dimethanol (CHDM), 15.25 mL (14.03 g) of N-methyl morpholine (NMM), and 50 mL of methylene chloride were transferred into a 250 mL flask equipped with a funnel. The solution in the flask was cooled down to −40° C. with stirring. A solution of 15.19 g of hexyl phosphoro dichloridate (HOP) in 20 mL of methylene chloride was added through the funnel, and an additional 10 mL of methylene chloride was used to flush through the funnel. The mixture was then brought up to room temperature gradually and kept stirring for four hours.

The reaction mixture was filtered, and the filtrate was evaporated to dryness. The residue was re-dissolved in 100 ml of chloroform. This solution was washed with 0.5 M mixture of HCl-NaCl solution, washed with saturated NaCl solution, dried over anhydrous $Na_2SO_4$, and quenched into a 1:5 ether-petroleum mixture. The resulting oily precipitate was collected and dried under vacuum to form a clear, pale yellow viscous material. The structure of the product was confirmed by $^1$H-NMR, $^{31}$P-NMR and FT-IR spectra.

Example 4
Synthesis of the Poly(phosphoester) P(trans-CHDM-BOP)

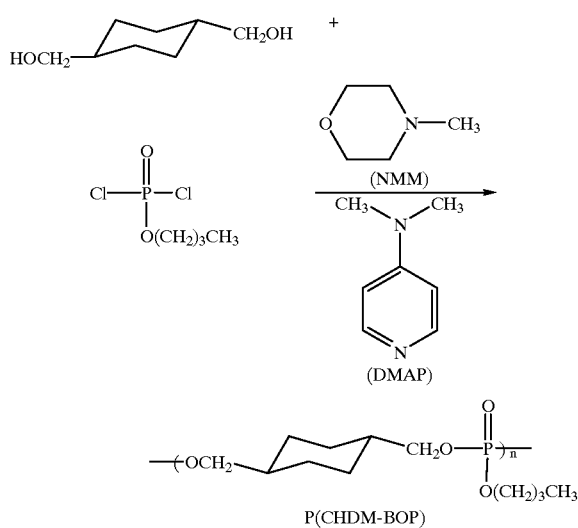

P(CHDM-BOP)

Under an argon stream, 10 g of trans-1,4-cyclohexane dimethanol (CHDM), 0.424 g (5%) of 4-dimethylamino-pyridine (DMAP), 15.25 mL (14.03 g) of N-methyl morpholine (NMM) and 50 mL of methylene chloride were transferred into a 250 mL flask equipped with a funnel. The solution in the flask was cooled down to −40° C. with stirring. A solution of 13.24 g of butyl phosphoro-dichloridate (BOP) in 20 mL of methylene chloride was added through the funnel, with an additional 10 mL of methylene chloride being used to flush through the funnel. The mixture was heated to the boiling point gradually, and kept refluxing for four hours. The reaction mixture was filtered, and the filtrate was evaporated to dryness, taking care to keep the temperature below 60° C. The residue was redissolved in 100 mL of chloroform. The solution formed was washed with 0.5 M of HCl-NaCl solution and saturated NaCl solution, dried over anhydrous $Na_2SO_4$, and quenched into a 1:5 ether-petroleum mixture. The resulting oily precipitate was collected and dried under vacuum to produce a clear, pale yellow viscous material.

Example 5
Synthesis of the Poly(phosphoester) P(trans-CHDM-EOP)

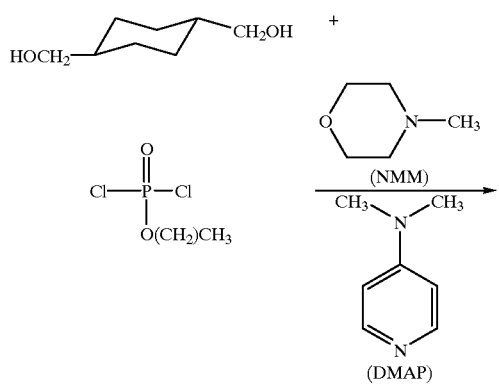

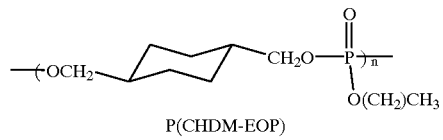

P(CHDM-EOP)

The polymer p(CHDM-EOP) was prepared by the method of Example 1 using, as starting materials, trans-1,4-cyclohexane dimethanol (CHDM) and ethyl phosphoro-dichloridate (EOP).

Example 6
Rheological Properties of P(trans-CHDM-HOP)

Figure 3A:
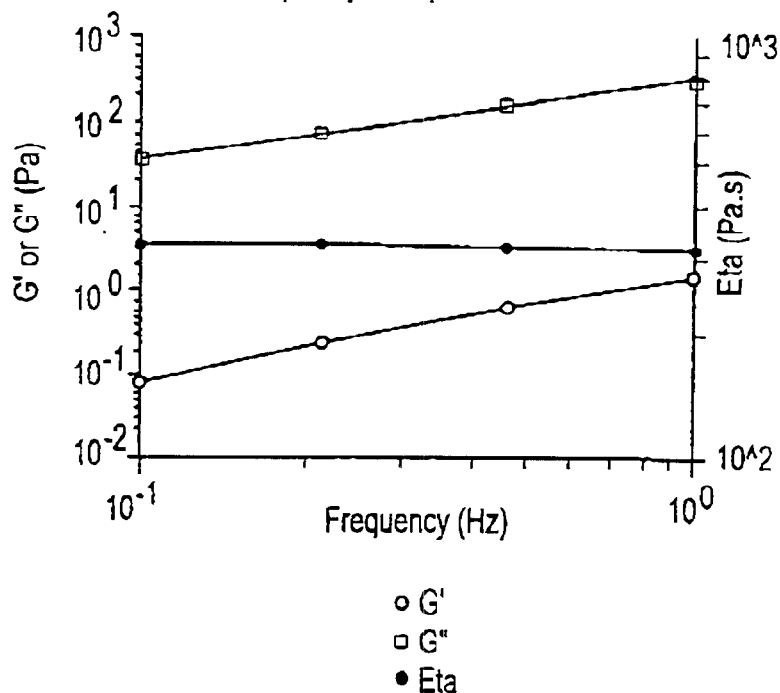
FIG. 3A graphically represents the active energy as a function of frequency of P(trans- CHDM-HOP)
Figure 3B:
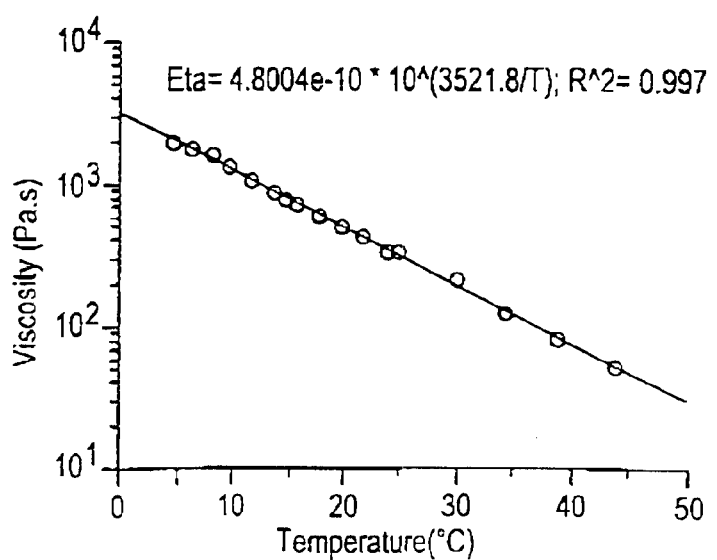
FIG. 3B shows temperature dependence of the corresponding viscosity.

P(trans-CHDM-HOP) remained in a flowable gel-like state at room temperature. The polymer exhibited a steady viscosity of 327Pa·s at 25° C. (shown in FIG. 3B), and a flowing active energy of 67.5 KJ/mol (shown in FIG. 3A).

Example 7
In Vitro Cytotoxicity of P(trans-CHDM-HOP)

Figure 4A:
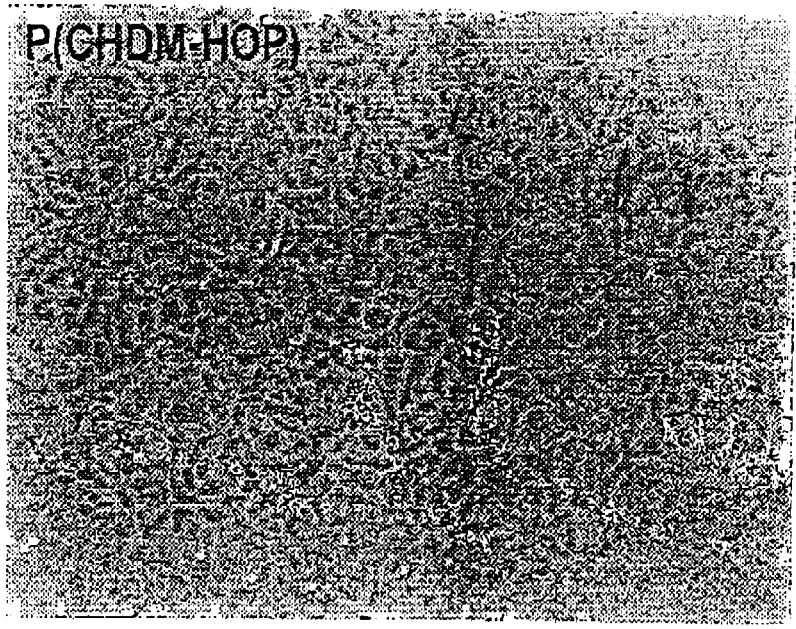
FIG. 4A shows HEK293 cells grown on a P(CHDM-HOP) surface after 72 hours of incubation.
Figure 4B:
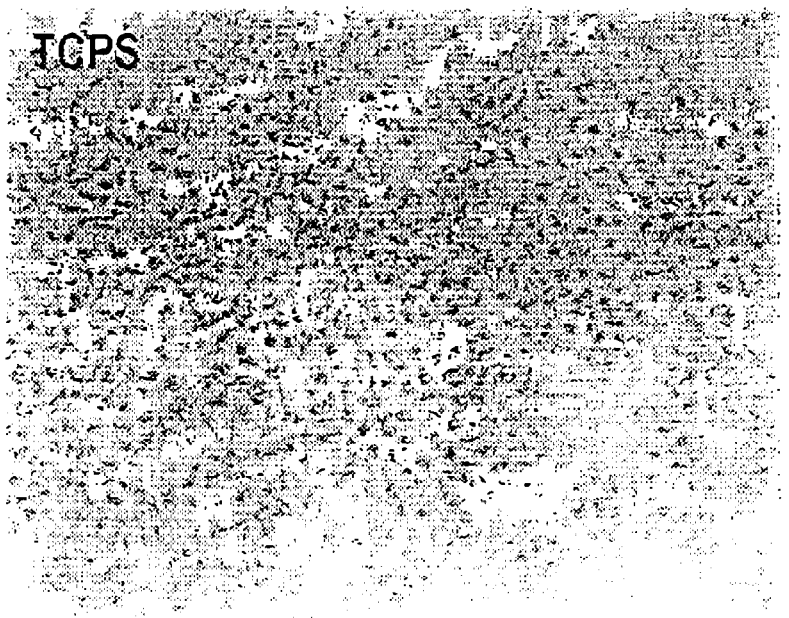
FIG. 4B shows HEK293 cells grown on a TCPS surface after 72 hours of incubation.

Cover slips were coated with P(trans-CHDM-HOP) by a spin coating method. The coated coverslips were then dried and sterilized by UV irradiation overnight under a hood. A P(trans-CHDM-HOP)-coated cover slip was placed at the bottom of each well of a 6-well plate. $5\times10^5$ HEK293 (human embryonic kidney) cells were plated into each well and cultured for 72 hours at 37° C. The resulting cell morphology was examined, using tissue culture polystyrene (TCPS) as a positive control. The cells growing on the P(CHDM-HOP) surface proliferated at a slightly slower rate. However, the morphology of cells grown on the polymer surface was similar to the morphology of cells grown on the TCPS surface. See FIG. 4A for the morphology of HEK293 cells grown on the polymer surface and FIG. 4B for the morphology of HEK293 cells grown on a TCPS surface, both after 72 hours of incubation.

Example 8
In Vitro Degradation of P(CHDM-Alkyl Phosphates)

Each of the following poly(phosphate)s was prepared as described above:

TABLE I

| Polymer | Side Chain |
|---|---|
| P(CHDM-HOP) | —O-hexyl group |
| P(CHDM-BOP) | —O-butyl group |
| P(CHDM-EOP) | —O-ethyl group |

Figure 5:
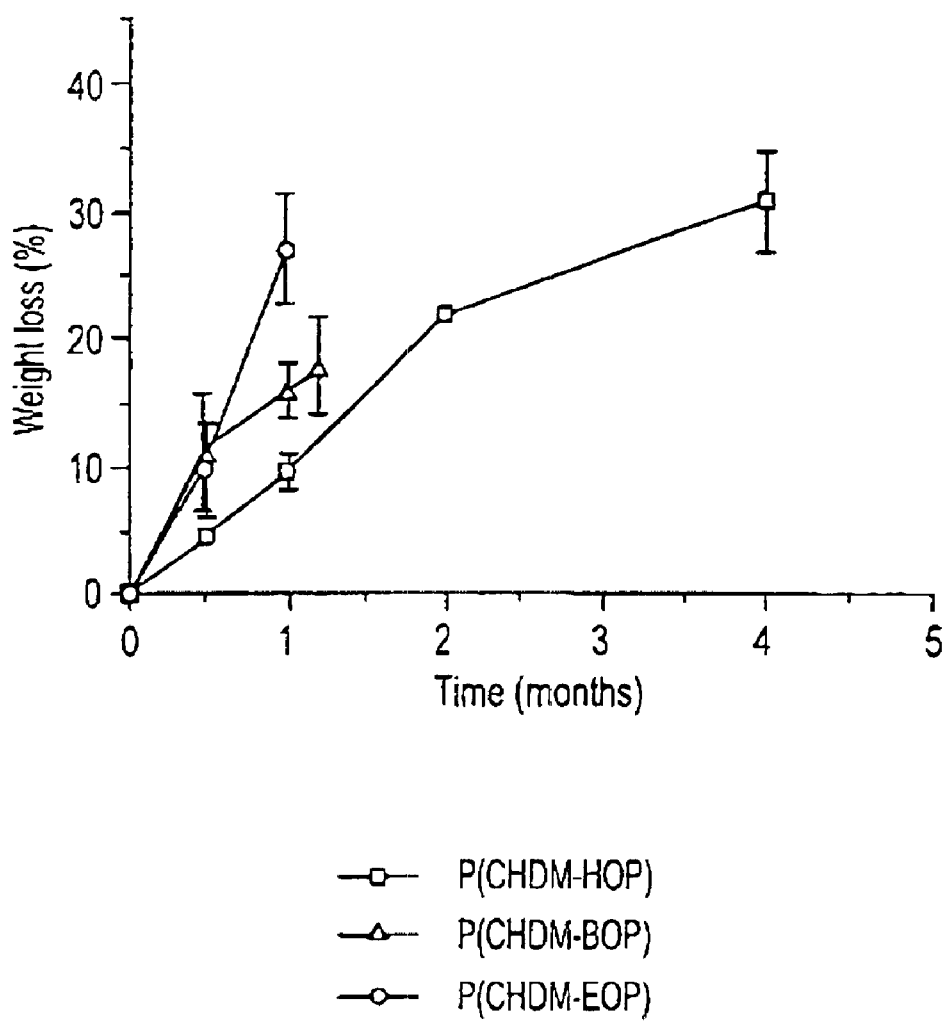
FIG. 5 graphically represents the effect of the side chain structure on the in vitro degradation rate of three poly(phosphoesters) of the invention in phosphate buffer solution.

A sample of 50 mg of each polymer was incubated in 5 mL of 0.1 M, pH 7.4 phosphate buffer saline (PBS) at 37° C. At various points in time, the supernatant was poured out, and the polymer samples were washed three times with distilled water. The polymer samples were then extracted with chloroform, and the chloroform solution was evaporated to dryness. The residue was analyzed for weight loss by comparing with the original 50 mg sample. FIG. 5 graphically represents the effect of the side chain structure on the in vitro degradation rate of poly(phosphates) in PBS.

Example 9

In Vitro Release Profile of Protein by P(CHDM-HOP)

Figure 6:
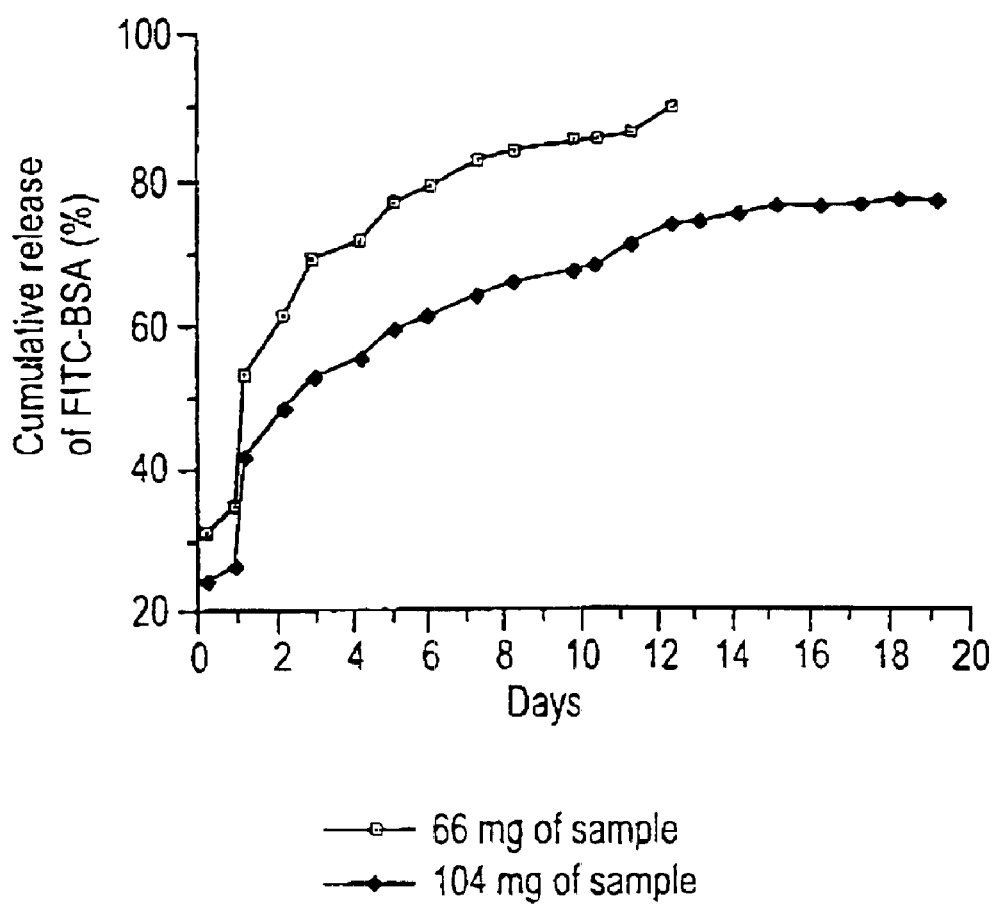
FIG. 6 shows the release curves of the bio-macromolecule FITC-BSA from the polymer P(CHDM-HOP) at 33% loading.

The polymer P(CHDM-HOP) was blended with the protein FITC-BSA (bovine serum albumin, a protein, tagged with the fluorescent label FITC; "FITC-BSA") at a 2:1 (w/w) ratio (33% loading). Measured amounts (66 mg or 104 mg) of the polymer-protein blend were placed into 10 ml of PBS (0.1M, pH 7.4), a phosphate buffer. At regular intervals (roughly every day), the samples were centrifuged, the supernatant buffer was removed and subjected to absorption spectroscopy (501 nm), and fresh amounts of buffer were added to the samples. The resulting release curve, plotting the cumulative percentage of FITC-BSA released versus time, is graphically represented in FIG. 6. The loading level of the protein in both cases was 33 weight %.

Example 10
In Vitro Protein Release Profile At Various Loading Levels

Figure 7:
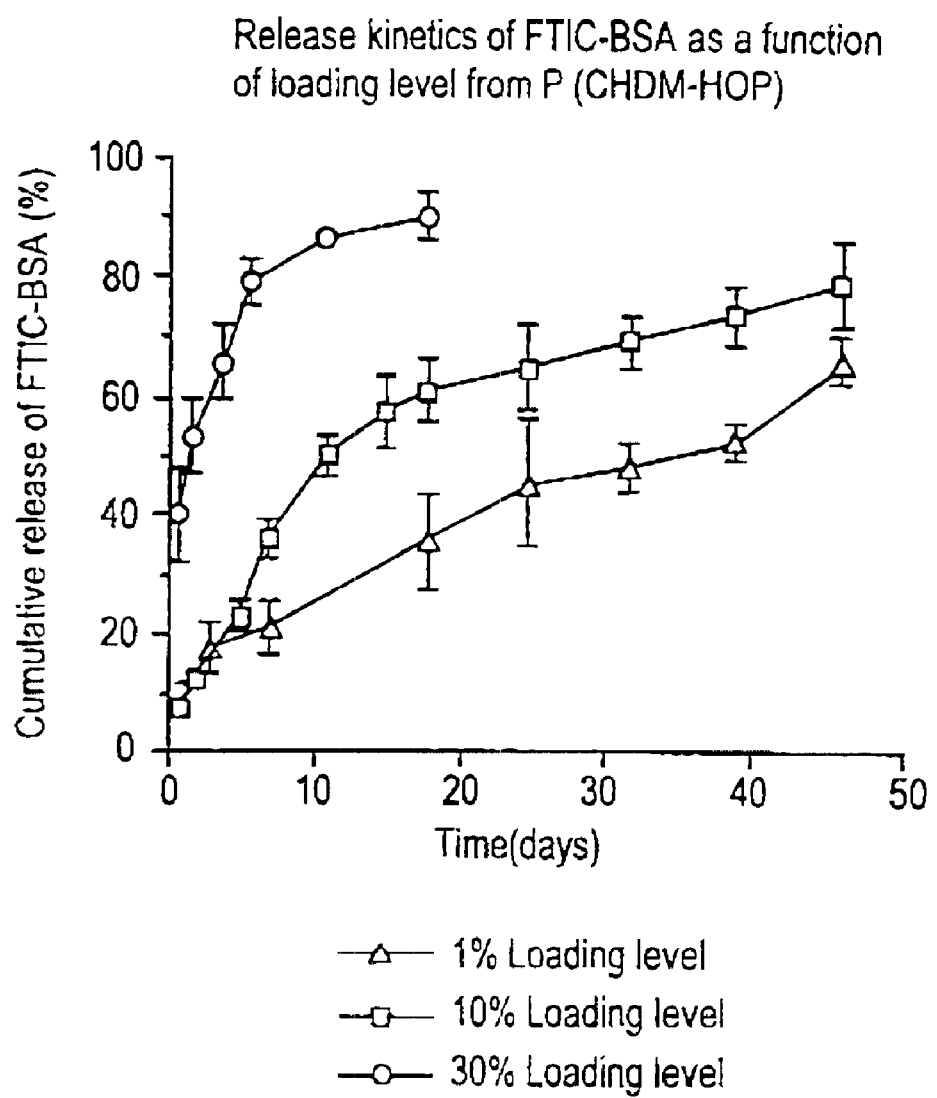
FIG. 7 graphically represents the in vitro release kinetics of FITC-BSA as a function of a loading levels of 30%, 10% and 1%.

FITC-BSA was blended with P(CHDM-HOP) at different loading levels (1%, 10% and 30%) at room temperature until the mixture formed a homogenous paste. 60 mg of the protein-loaded polymer paste was placed in 6 mL of 0.1 M phosphate buffer and constantly shaken at 37° C. At various time points, samples were centrifuged, and the supernatant was replaced with fresh buffer. The released FITC-BSA in the supernatant was measured by UV spectrophotometry at 501 nm. FIG. 7 graphically represents the in vitro release kinetics of FITC-BSA as a function of loading level.

Example 11
Effect of Side Chain Structure on In Vitro Protein Release Kinetics of FITC-BSA The following three polymers were prepared as described above:

P(CHDM-EOP)

P(CHDM-BOP) and

P(CHDM-HOP)

Figure 8:
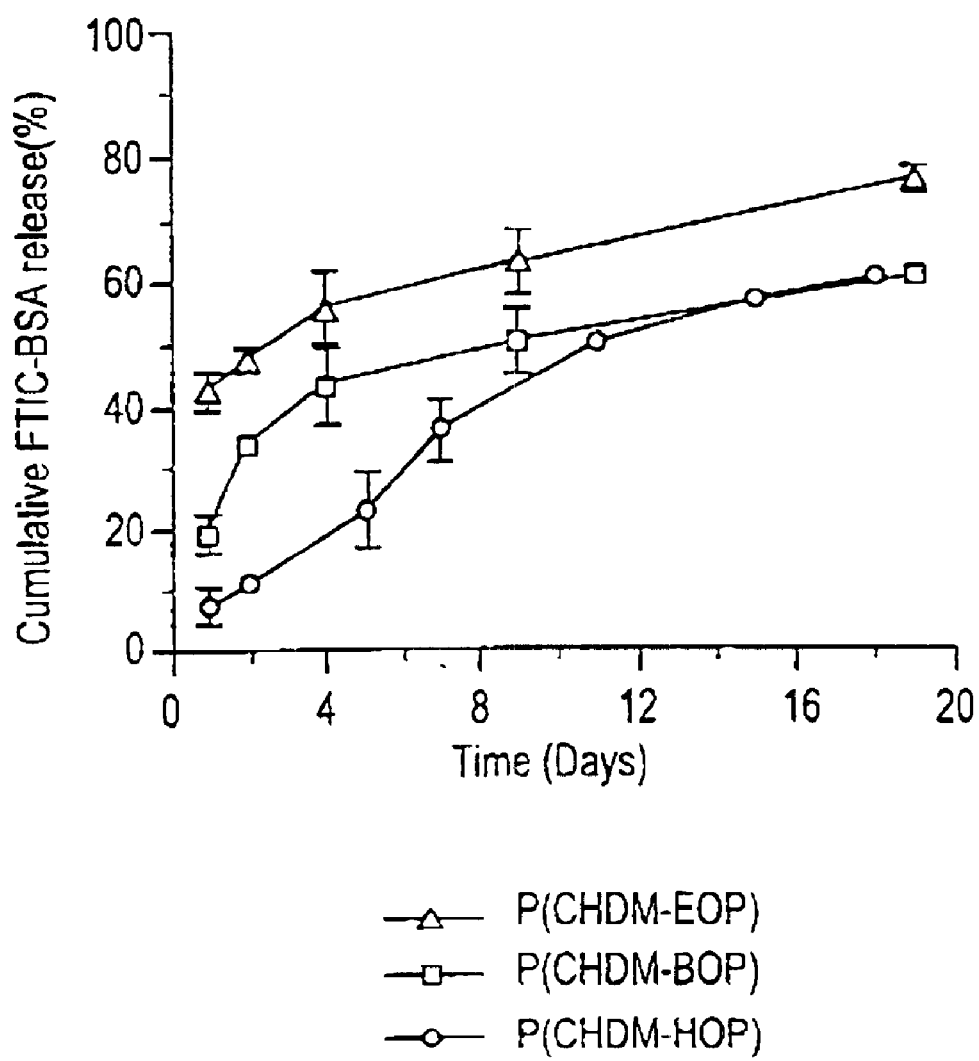
FIG. 8 graphically represents the in vitro effect of side chain structure on the protein release kinetics of FITC-BSA with a 10% loading level.

FITC-BSA was blended with each polymer at a 10% loading level at room temperature to form a homogenous paste. 60 mg of the protein-loaded polymer paste was placed in 6 mL of 0.1 M phosphate buffer with constant shaking at 37° C. At various time points, samples were centrifuged, and the supernatant was replaced with fresh buffer. The released FITC-BSA in the supernatant was measured by UV spectrophotometry at 501 nm. FIG. 8 graphically represents the in vitro effect of side chain variations on the protein release kinetics of FITC-BSA at 10% loading level.

Example 12
In Vitro Small Molecular Weight Drug Release from P(CHDM-HOP)

Figure 9:
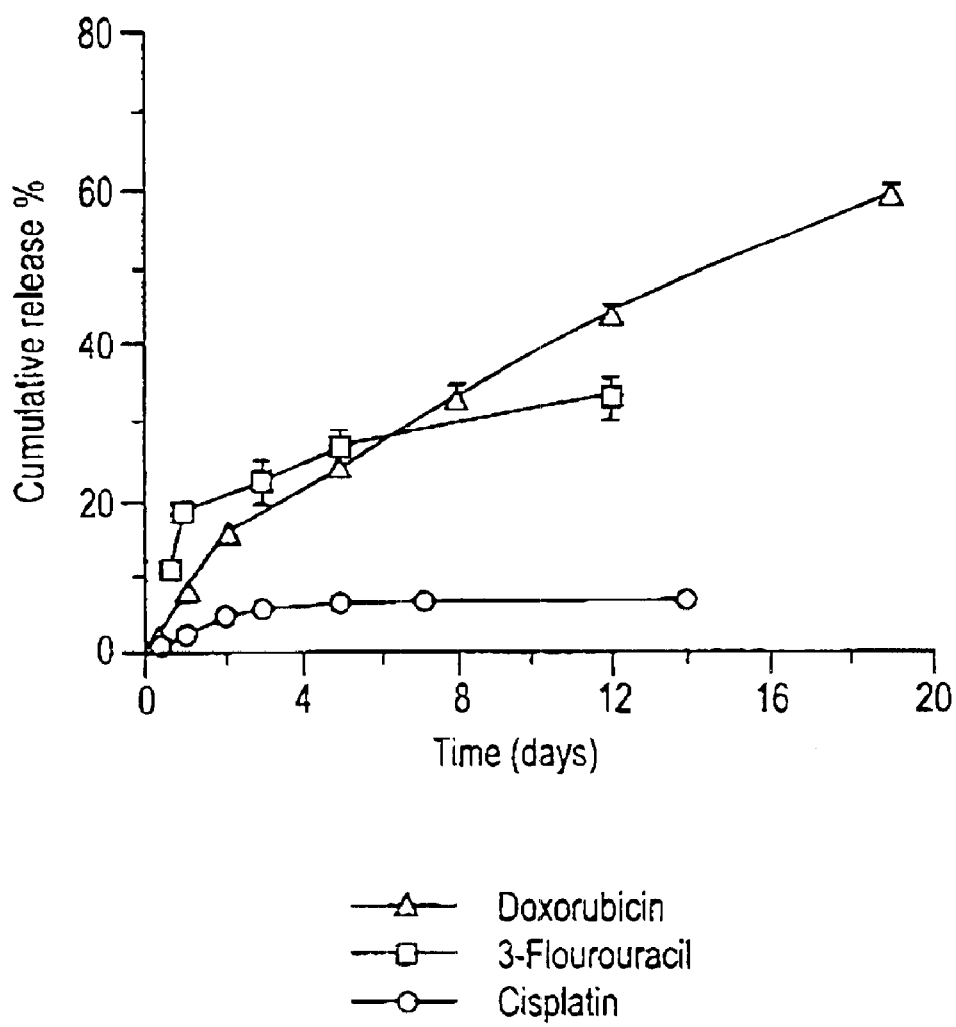
FIG. 9 shows the release of low molecular weight drugs (doxorubicin, cisplatin, and 5-fluorouracil) from P(CHDM-HOP).

A P(CHDM-HOP) paste containing doxorubicin, cisplatin, or 5-fluorouracil, was prepared by blending 100 mg of P(CHDM-HOP) with 1 mg of the desired drug at room temperature, respectively. An aliquot of 60 mg of the drug-loaded paste was placed in 6 mL of 0.1 M phosphate buffer at 37° C. with constant shaking, with three samples being done for each drug being tested. At various time points, the supernatant was replaced with fresh buffer solution. The levels of doxorubicin and 5-fluorouracil in the supernatant were quantified by UV spectrophotometry at 484 nm and 280 nm, respectively. The cisplatin level was measured with an atomic absorbance spectrophotometer. FIG. 9 shows the release of these low molecular weight drugs from P(CHDM-HOP).

Example 13
In Vitro Simultaneous Release Profile of Doxorubicin and Cisplatin from P(CHDM-HOP)

Figure 10:
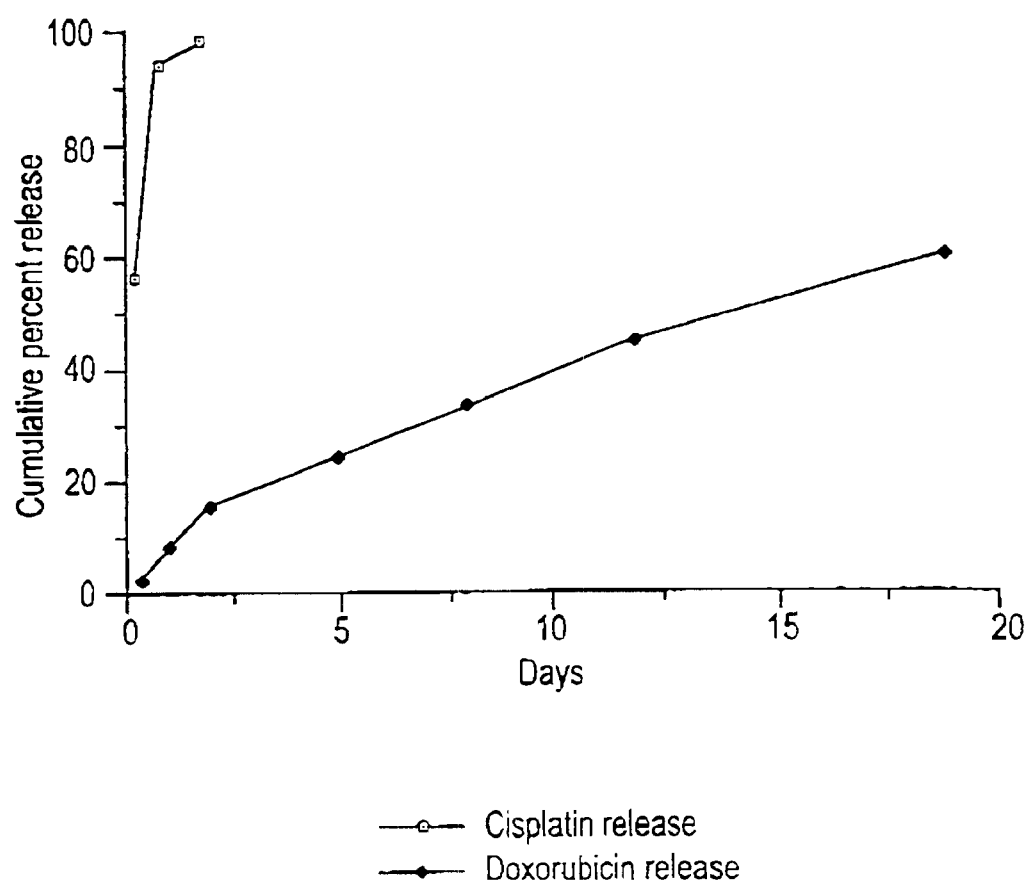
FIG. 10 graphically represents the simultaneous release of cisplatin and doxorubicin from a P(CHDM-HOP) matrix.

A paste was made by blending 300 mg of P(CHDM-HOP) with 6 mg of doxorubicin and 6 mg of cisplatin at room temperature to form a uniform dispersion. A sample of 100 mg of the paste was incubated in 10 mL of phosphate buffer (pH 7.4) at 37° C. with shaking. At different time points, samples were centrifuged, 9 mL of the supernatant were withdrawn and replaced with fresh buffer. The withdrawn supernatant was assayed spectrophotometrically at 484 nm to determine the amount of doxorubicin released into the withdrawn supernatant, and the cisplatin release was measured by atomic absorbance spectrophotometer. FIG. 10 graphically represents the simultaneous release of cisplatin and doxorubicin from P(CHDM-HOP).

Example 14
In Vitro Interleukin-2 Release from P(CHDM-HOP)

Figure 11:
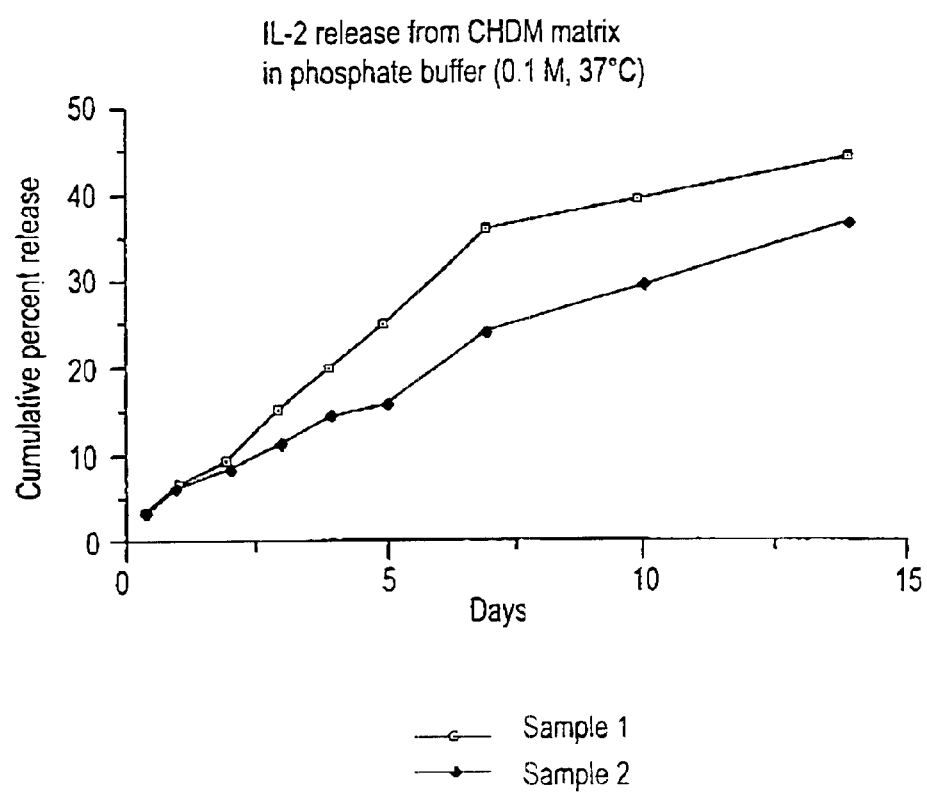
FIG. 11 graphically represents the cumulative percentage of released IL-2 from the P(CHDM-HOP) matrix in phosphate butter as a function of time.

A paste was prepared by blending, with a spatula, 330 mg of P(CHDM-HOP) with 3 mg of IL-2 at room temperature to form a uniform dispersion. A sample of 95 mg of the P(CHDM-HOP)/IL-2 paste was placed in 5 mL of 0.1 M phosphate buffer (pH 7.4) at 37° C. At various time points, the sample was centrifuged and 4 mL of the supernatant of 4 mL was withdrawn and replaced. the withdrawn supernatant was assayed for IL-2 by use of CTLL-2 culture, as described above. The cumulative percentage of IL-2 released was calculated based on the initial amount of IL-2 blended into the paste. At the last time point, there was IL-2 still left in the sample. FIG. 11 graphically represents the cumulative percentage of released IL-2 from the P(CHDM-HOP) matrix versus time in days.

Example 15
In Vitro Release of Interleukin-2 from P(CHDM-HOP) in Tissue Culture

A paste was prepared by blending, with a spatula, lyophilized human Interleukin-2 ("IL-2", $18 \times 10^6$ IU) with 240 mg of P(CHDM-HOP) at room temperature until homogeneous. Three 80 mg samples of the P(CHDM-HOP)/IL-2 paste were incubated with 1.5 mL of tissue culture (RPMI1640 Medium containing 10% FCS) at 37° C. with constant shaking. At various time points, the samples were centrifuged, and the supernatant was withdrawn and replaced with fresh medium. The amount of IL-2 in the withdrawn supernatant samples was determined by an ELISA assay.

Figure 12A:
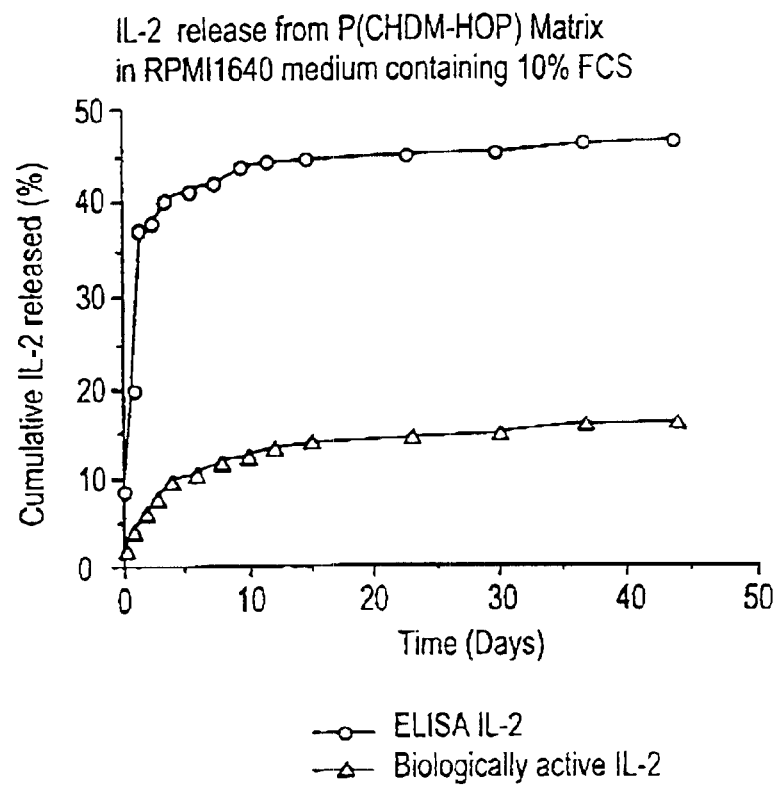
FIG. 12 shows the calibration curves for the cumulative percentage release of IL-2 from a P(CHDM-HOP) matrix in phosphate buffer.
Figure 12B:
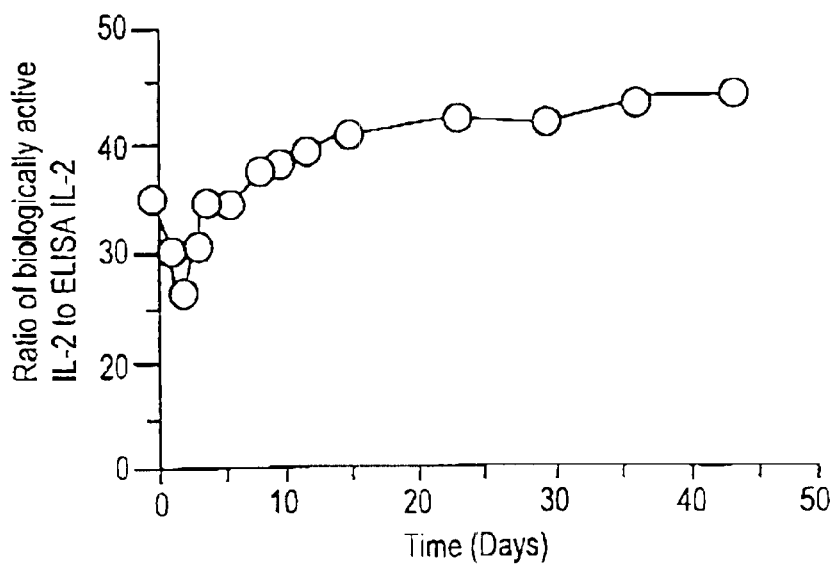

The amount of biologically active IL-2 released was assayed by the following CTLL cell culture method: CTLL cells were plated in a 96-well plate at a density of $2 \times 10^4$ cells per well and incubated with an aliquot of the withdrawn supernatant. After two days of incubation, the rate of cell growth was evaluated by WST-1 assay. A calibration curve was constructed in parallel for the assay of IL-2 release from P(CHDM-HOP) in tissue culture medium. FIG. 12 shows the calibration curves constructed by the sustained release of IL-2. The complete data establish that more than 30% of the bioactivity was retained at all points in time.

Example 17
In Vivo Release of Interleukin-2 from P(CHDM-HOP)

A sample of P(CHDM-HOP) was sterilized by γ-irradiation at 2.5 MRads and aseptically blended with IL-2 in the same manner as described above in Example 15. Six female Balb/c mice, 6–8 weeks of age, were injected subcutaneously with 50 mg of the IL-2 polymer paste sample containing $3.5 \times 10^5$ IU of IL-2. Two additional mice received the same dose of IL-2 as a bolus injection, and two additional mice received blank P(CHDM-HOP) injection as a control.

Figure 13:
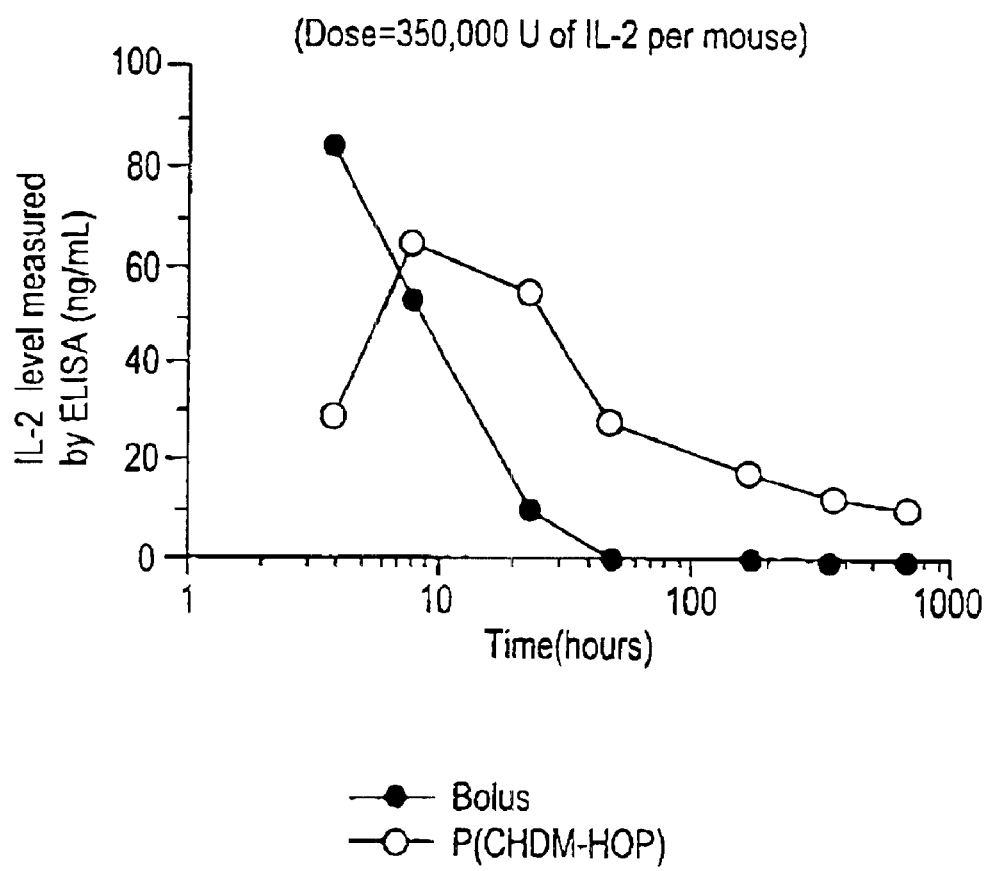
FIG. 13 compares the pharmacokinetics of IL-2 administered as a subcutaneous bolus or dispersed in a P(CHDM-HOP) matrix.
Figure 14:
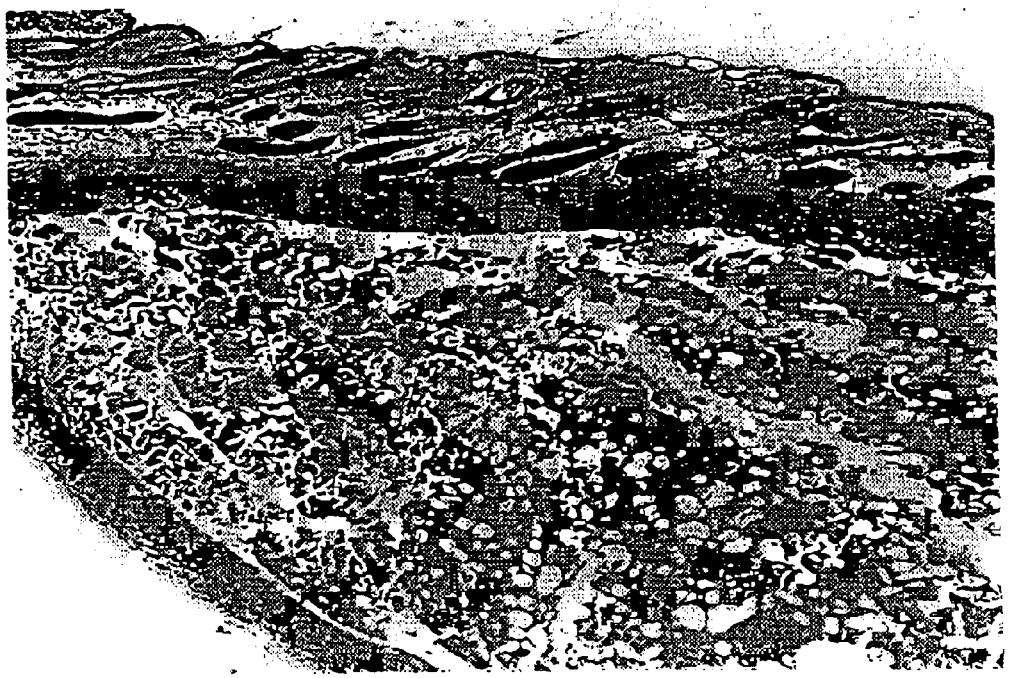
FIG. 14 shows the results of a histological examination of a subcutaneous injection site in a Balb/c mouse.

At various time points, 50 µL of blood samples were collected from the tail vein. Blood samples from each group were combined and diluted with HBSS supplemented with 1% BSA. The serum was separated and assayed for IL-2 as described above. Sustained release of IL-2 was attained in vivo, with detectable levels of IL-2 present in the serum, for up to three weeks after injection of the P(CHDM-HOP)/IL-2-loaded paste. In contrast, the IL-2 levels were undetectable after 48 hours in the mice injected with the IL-2 bolus. FIG. 13 graphically compares the pharmacokinetics of IL-2 administered either as a bolus or dispersed in a P(CHDM-HOP) matrix. FIG. 14 depicts the histological examination of a subcutaneous injection site from this in vivo experiment.

Example 18
In Vivo Biocompatibility of P(trans-CHDM-HOP)

The polymer P(trans-CHDM-HOP) was synthesized as described in Example 1. To facilitate injection, ethyl alcohol was added to the polymer at levels of 10% and 20% by volume to reduce the viscosity. Samples of 25 $\mu L$ of the polymer alone, 25 $\mu L$ of the polymer containing 10% alcohol, and 25 $\mu L$ of the polymer containing 20% alcohol, were injected into the back muscles of Sprague Dawley rats. Tissues at the injection sites were harvested at either three or thirteen days post-injection, processed for paraffin histology, stained with heamatoxylln, eosin dye and analyzed. Medical-grade silicon oil was injected into the control group rats.

Histological examination of the back muscle sections of the rats injected with the polymer diluted with ethanol showed no acute inflammatory response. The level of macrophage presence was comparable to that of the control group, which had been injected with medical-grade silicon oil, and neutrophils were not present in any of the samples taken on either the third or thirteenth day.

Example 18
Drug Sensitivity in an In Vitro Tumor Model

In vitro studies were done on the melanoma cell line B16/F10 using, as the drug, doxorubicin ("DOX"), cisplatin, or 5-fluorouracil ("5-FU"). The B16/F10 cells were cultivated in the presence of different concentrations of DOX, cisplatin and 5-FU. According to the data, DOX showed the strongest inhibitory effect on the cell culture, even at 0.1 $\mu g/mL$.

Example 19
Controlled Delivery of Interleukin-2 and Doxorubicin from P(CHDM-HOP) in an In Vivo Tumor Model Lyophilized interleukin-2 ("IL-2") was purchased from Chiron, mouse Interferon-$\gamma$ ("mIFN-$\gamma$") was obtained from Boehringer Mannheim, and doxorubicin hydrochloride ("DOX") was obtained from Sigma. C57BL/6 mice, 6–8 weeks of age, were obtained from Charles River. The aggressive melanoma cell line B16/F10 was used to cause tumors in the mice, and the cells were maintained by weekly passages. The polymer P(CHDM-HOP) was synthesized as described in Example 1.

Mice were randomly allocated into groups as shown below in TABLE II. The day of tumor injection with cells of the melanoma cell line was denoted as Day 0. Each mouse received a subcutaneous injection of 50 $\mu l$ ($10^5$) tumor cells in phosphate buffer saline (PBS) in the left flank. On Day 3 or Day 7, the tumor-bearing mice were selectively injected in the right flank with one of the following formulations: (1) a bolus of IL-2, (2) a bolus of DOX, (3) a polymer paste of IL-2, (4) a polymer paste of DOX, (5) a polymer paste containing both IL-2 and DOX, or (6) a polymer paste containing both IL-2 and mIFN-$\gamma$. A control group and negative control group received no further injections on Day 3 or Day 7.

The bolus preparation of either IL-2 or DOX was prepared by dissolving an appropriate amount of IL-2 or DOX in 50 $\mu l$ of isotonic solution just prior to the injection. The polymer paste formulations of either IL-2, DOX, a mixture of both IL-2 and DOX, or a mixture of IL-2 and mIFN-$\gamma$, were prepared by blending 50 $\mu l$ of sterilized P(CHDM-HOP) with the drug(s) until homogeneous.

TABLE II

Allocation of Groups of Mice for In Vivo Tumor Model

| Group | Number of Mice | Day of Injection | Formulation |
|---|---|---|---|
| Control | 5 | — | Nothing |
| Negative Control | 5 | — | Nothing |
| Bolus IL-2 | 8 | 3 | $0.8 \times 10^6$ IU |
| Bolus DOX | 8 | 3 | 0.5 mg |
| Bolus DOX | 8 | 7 | 0.5 mg |
| Paste IL-2 | 10 | 3 | $0.8 \times 10^6$ IU |
| Paste IL-2 | 10 | 7 | $0.8 \times 10^6$ IU |
| Paste DOX | 10 | 3 | 0.5 mg |
| Paste DOX | 10 | 7 | 0.5 mg |
| Paste (IL-2 + DOX) | 10 | 3 | $0.8 \times 10^6$ IU + 0.5 mg |
| Paste (IL-2 + DOX) | 10 | 7 | $0.8 \times 10^6$ IU + 0.5 mg |
| Paste (IL-2 + mIFN-$\gamma$) | 10 | 3 | $10^6$ IU |

On Day 28 and Day 42 of tumor growth, the tumor sizes of the various mice were measured. The results are shown below in Table III, which shows the numerical data for the growth of tumor volumes on Day 28 and Day 42 and the number of mice who survived the experiment per drug grouping. Tumor volume was calculated as half the product of the length and the square of the width, in accordance with the procedure of Osieka et al., 1981.

TABLE III

CHDM-HOP Polymer as Carrier for Cytokine and Drug Delivery in Melanoma Model

| Group | Initial Number of Mice | Tumor Volume (mm$^3$ ± SEM*) After Tumor Injection | |
|---|---|---|---|
| | | 28 days | 42 days |
| | | Number of Mice Survived | |
| Control | 5 | No tumor | No tumor |
| Negative Control | 5 | 2458 ± 1070.7 / 4 | 5656 / 1 |
| Bolus IL-2 (3d) | 8 | 1946 ± 505.6 / 8 | 3282 ± 1403.3 / 4 |
| Bolus Dox (3d) | 8 | 1218.9 ± 304.1 / 8 | 3942.5 ± 1818 / 5 |
| Bolus Dox (7d) | 8 | 1661.2 ± 301.8 / 8 | 4394.3 ± 741.3 / 3 |
| Paste IL-2 (3d) | 10 | 934.1 ± 230 / 10 | 3183 ± 1223.4 / 5 |
| Paste IL-2 (7d) | 10 | 2709.8 ± 397.3 / 10 | 10491 ± 2485.5 / 3 |
| Paste Dox (3d) | 10 | 1410 ± 475.3 / 8 | 4648.9 ± 1202.2 / 7 |
| Paste Dox (7d) | 10 | 1480 ± 287 / 9 | 3915 ± 1739.7 / 4 |
| Paste (IL-2 + DOX) (3d) | 10 | 657.3 ± 248.9 / 8 | 3362.8 ± 1120.1 / 7 |
| Paste (IL-2 + DOX) (7d) | 10 | 857.2 ± 243.6 / 8 | 3449.8 ± 1285.9 / 5 |

TABLE III-continued

CHDM-HOP Polymer as Carrier for Cytokine
and Drug Delivery in Melanoma Model

| Group | Initial Number of Mice | Tumor Volume (mm$^3$ ± SEM*) After Tumor Injection | |
|---|---|---|---|
| | | 28 days | 42 days |
| | | Number of Mice Survived | |
| Paste (IL-2 + mIFN-γ) (3d) | 10 | 1217.9 ± 168.49 | 4469.8 ± 2018.74 |

*Standard Error of the Mean

Figure 15:
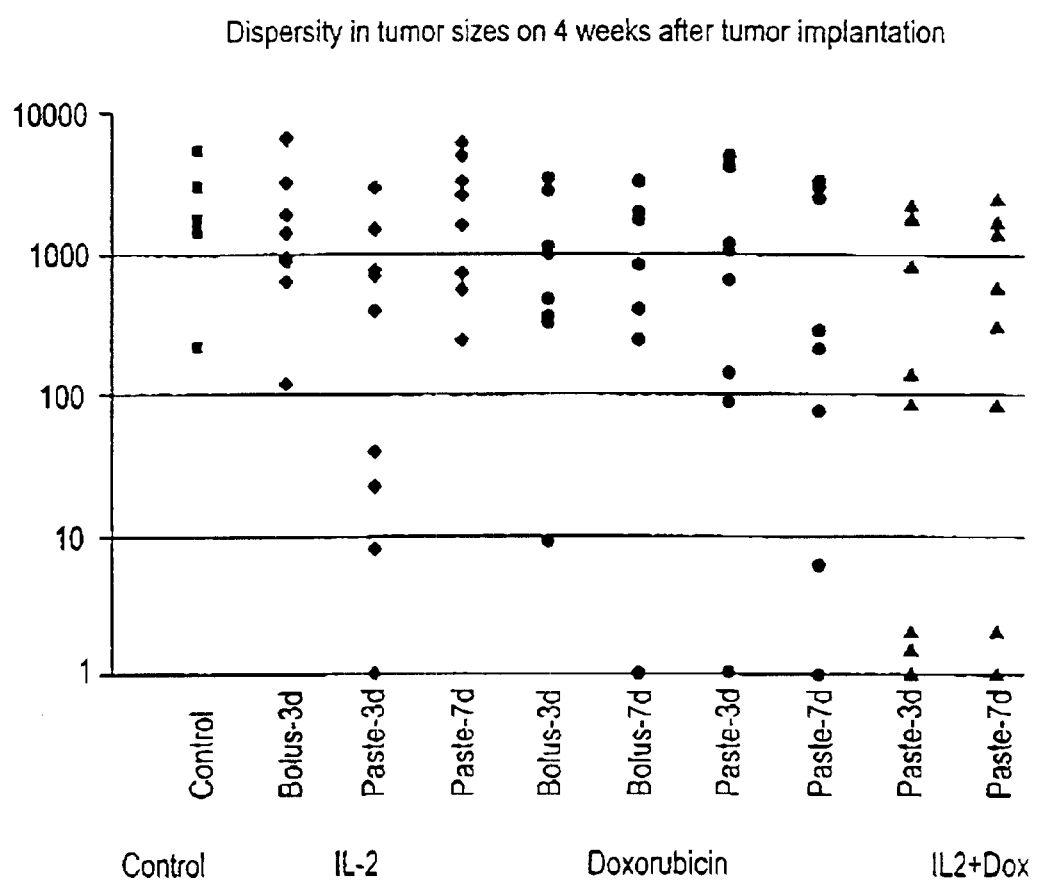
FIG. 15 shows the distribution of tumor sizes in mice four weeks after tumor implantation in an in vivo melanoma tumor model.
Figure 16:
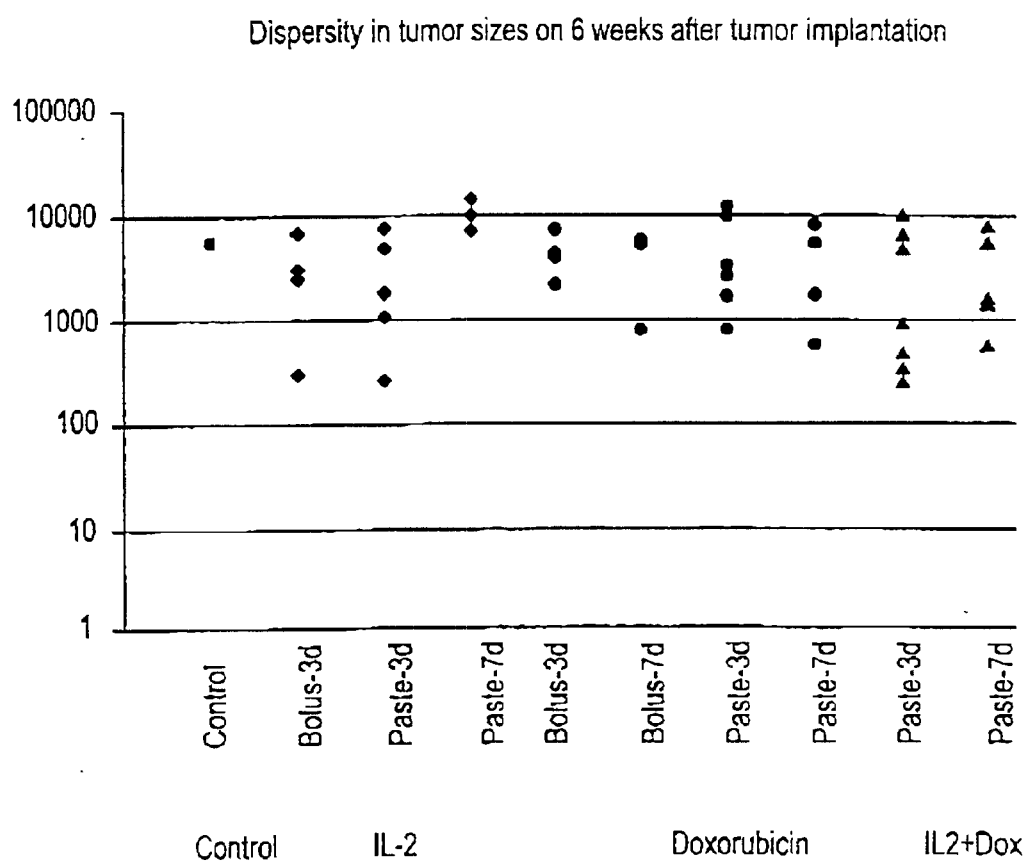
FIG. 16 shows the distribution of tumor sizes in mice six weeks after tumor implantation in an in vivo melanoma tumor model.

Based on these measurements, the distribution of tumors sizes were graphically represented in FIG. 15 for Day 28 (four weeks after tumor implantation) and in FIG. 16 for Day 42 (six weeks after tumor implantation). The graphs were subdivided into plots according to the different treatments given to the tumor-bearing mice.

The results on Day 28 showed that, in comparison with the control group (tumor without treatment) and the bolus injection of IL-2, the group of mice receiving a polymer/IL-2 paste injection successfully delayed the tumor's growth. However, for the group of mice not receiving a polymer/IL-2 paste injection until Day 7, the tumor had already become of substantial size by Day 7 and, accordingly, a significant reduction in tumor size was not observed.

Excellent tumor reduction was obtained with the combination of IL-2 and DOX. The average size of a tumor treated with an injection of a polymer paste containing both IL-2 and DOX was significantly smaller than the tumor in the control group. Specifically, the average tumor size for mice receiving the IL-2 and DOX/polymer paste on Day 3 was 657.3 mm$^3$ as opposed to 2458 mm$^3$ for the control group. Even when treatment was delayed until Day 7 of tumor growth, a therapeutic effect could still be seen with the polymer paste formulation containing both IL-2 and DOX.

The results on Day 42 of tumor growth also confirmed that the Day 3 injection of polymer paste containing both IL-2 and DOX gave the best result in delaying tumor growth. The combined therapy of IL-2 and DOX in a polymer paste of the invention resulted in the occurrence of smaller sized tumors in more of the test animals. According to the distribution data shown in FIG. 15, there were four mice bearing tumors of less than 1000 mm$^3$ in the case of the combined IL-2 and DOX polymer paste therapy, as compared with only one mouse inside that range for the polymer paste injection of DOX alone. It was also clear that IL-2 alone did not provide the most desirable effect, as evaluated on the 42nd day of tumor growth. Despite the good distribution of small tumor sizes on the 28th day, the long-time survival data appeared to be adversely affected, not only by the progression of tumor growth at that point, but also by the lack of continued, controlled delivery of IL-2 over a longer time period. With the polymer paste formulation of both IL-2 and DOX, the polymer degraded slowly, allowing a gradual decrease in the diffusion rate of the therapeutic agent over time.

Figure 17:
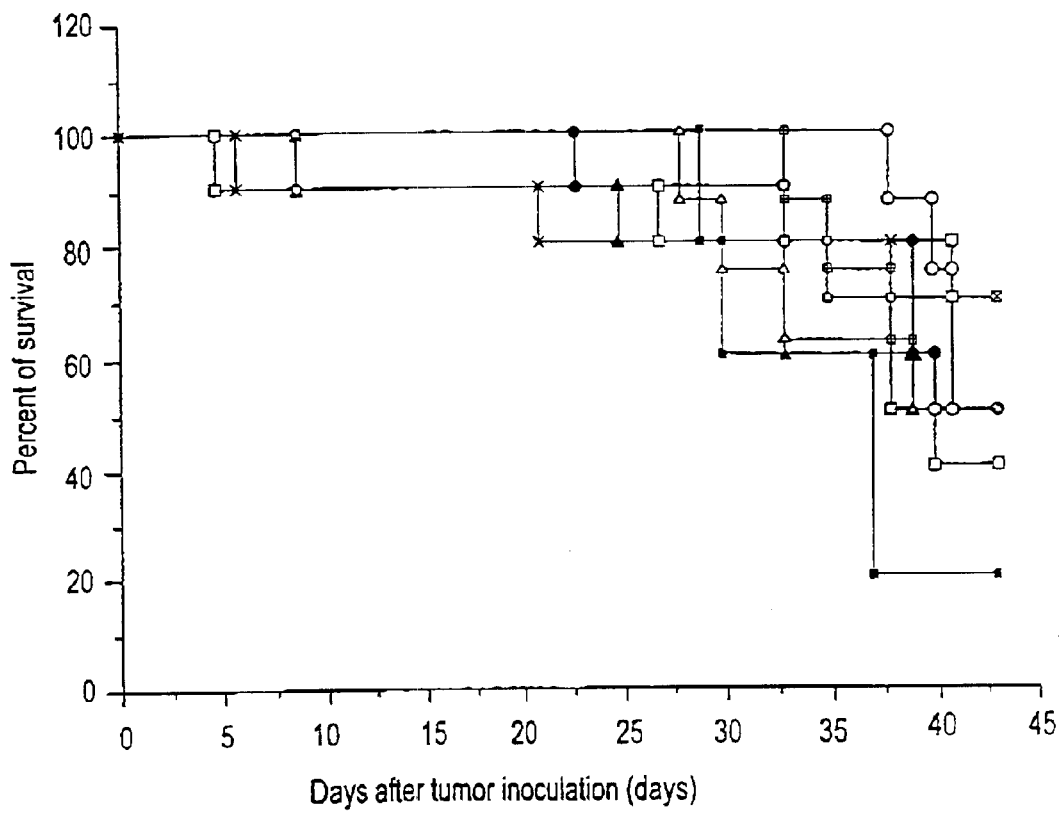
FIG. 17 shows the percentage of survival as a function of time for four different treatment groups in an in vivo melanoma tumor model.

However, because of the significant difference of the distribution in tumor sizes inside each group, the average tumor size as seen in TABLE III did not provide a complete picture. A fuller appreciation of the significance of the treatments of the invention can be gained by comparing data from the distribution graph of FIG. 16, which shows the dispersity in tumor sizes six weeks after tumor implantation, with the survival curve shown in FIG. 17, which shows the massive death of mice in all groups before the Day 42 measurement, except for the groups of animals that had received the 3rd day injection of paste containing either DOX alone or the combination of IL-2 and DOX. Thus, the data, taken as a whole, shows that the combined therapy of IL-2 and DOX in the paste both significantly delayed tumor growth and extended life.

Early deaths about 3–4 days after the injections of the DOX-containing polymer paste were thought to be due, at least in part, to the toxic effect of DOX causing the deaths of the weaker animals. Corresponding injections of bolus DOX did not produce early death, probably because of the rapid distribution and clearance from the body of the bolus-injected DOX.

Example 20
Incorporating Paclitaxel into P(CHDM-HOP) or P(CHDM-EOP)

100 mg of each of the polymers of Example 1, p(CHDM-HOP), and Example 5, p(CHDM-EOP), was dissolved in ethanol at a concentration of about 50%. After the polymer was completely dissolved, 5 mg of paclitaxel powder (a chemotherapeutic drug) was added to the solution and stirred until the powder was completely dissolved. This solution was then poured into ice water to precipitate the polymer composition. The resulting suspension was centrifuged, decanted, and lyophilized overnight, to obtain a viscous gel-like product.

Example 21
In Vitro Release of Paclitaxel from P(CHDM-HOP) and P(CHDM-EOP)

In a 1.7 mL plastic micro centrifuge tube, 5 mg of both of the paclitaxel polymer formulations of Example 20 to be tested was incubated with 1 mL of a buffer mixture of 80% PBS and 20% PEG 400 at 37° C. Four samples of each formulation to be tested were prepared. At specific time points, approximately every day, the PBS:PEG buffer was poured off for paclitaxel analysis by HPLC, and fresh buffer was added to the microcentrifuge tube. The release study was terminated at day 26, at which point the remaining paclitaxel in the polymer was extracted with a solvent to do a mass balance on paclitaxel.

Figure 18:
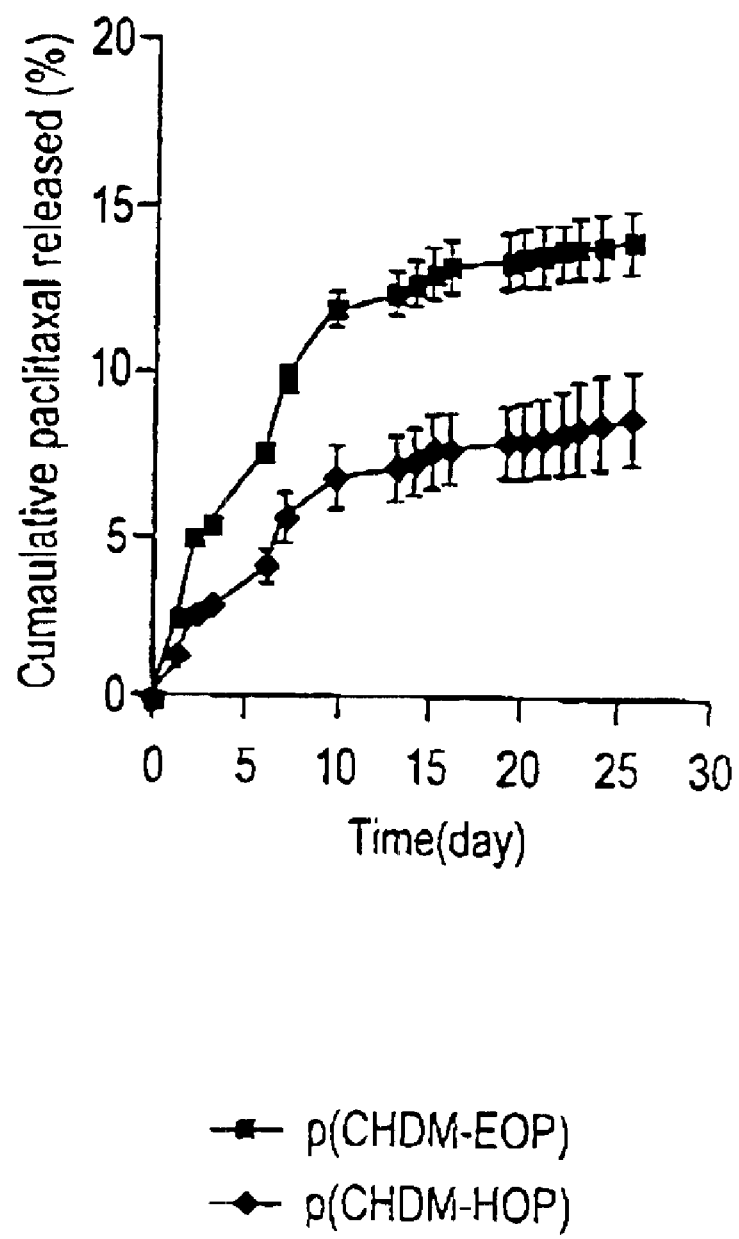
FIG. 18 shows the release curves of two polymer compositions of the invention, one comprising the chemotherapeutic agent paclitaxel in the polymer P(CHDM-EOP) and the other comprising paclitaxel in the polymer P(CHDM-HOP).

The resulting release curves for the release of paclitaxel from both polymers are shown in FIG. 18. The total paclitaxel recovery was 65% for the P(CHDM-HOP) formulation and 75% for the P(CHDM-EOP) formulation.

Example 22
Preparation of P(CHDM-HOP)/Lidocaine Paste

A paste of P(CHDM-HOP) and lidocaine (base; Sigma, Cat. # L-7757) was prepared by mechanically mixing as follows: 60 mg of P(CHDM-HOP) and 16 mg of lidocaine were weighed onto a glass microscope slide. The polymer and the lidocaine drug were thoroughly mixed with a spatula until a uniform mixture was obtained. The resulting lidocaine/polymer mixture formed a 24% w/w lidocaine paste with the lidocaine remaining as a solid.

Example 23
In Vitro Release of Lidocaine from P(CHDM-HOP)

Approximately 10 mg of the lidocaine/polymer mixture prepared above in Example 22 was placed in 2.0 mL of phosphate buffered solution (PBS) (0.1 M, pH 7.4) at 37° C. on a shaker. The buffer was replaced at specific time points, and samples were withdrawn. The lidocaine released from the polymer into the samples was assayed by HLPC.

Figure 19:
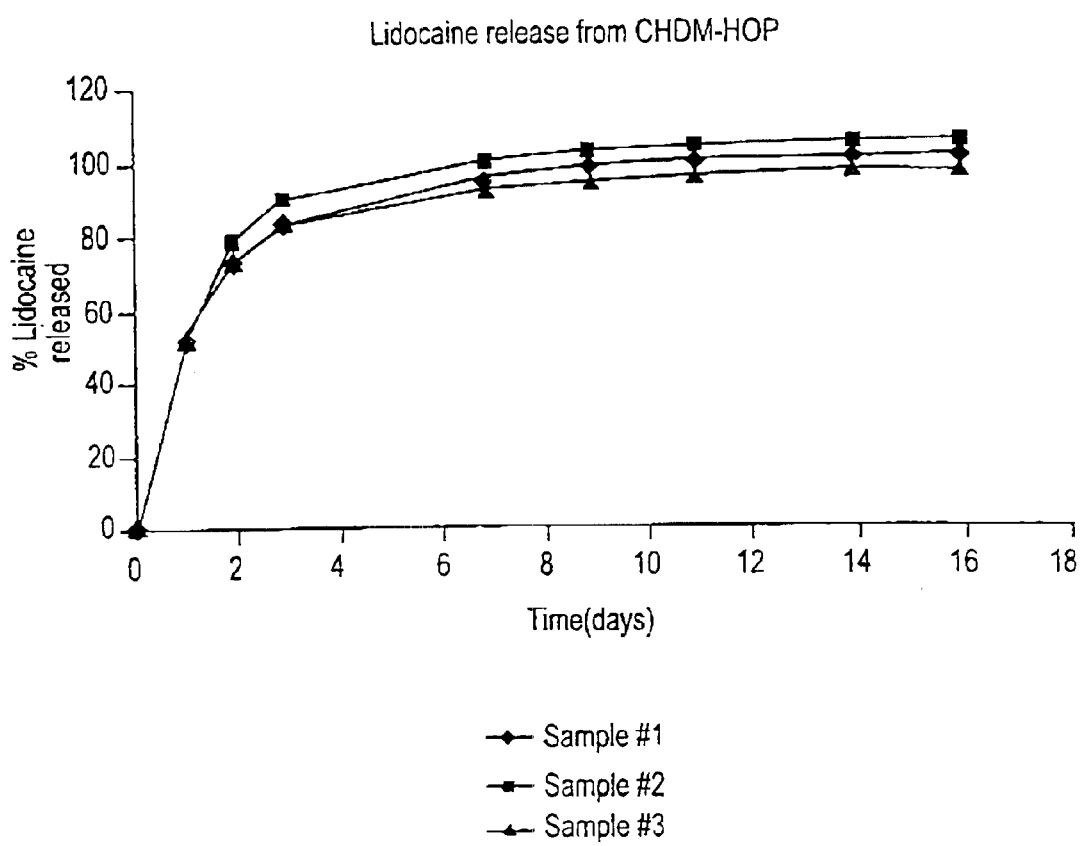
FIG. 19 shows the in vitro release curves of lidocaine from three different samples of P(CHDM-HOP)/lidocaine mixture.

The results of three different samples of the lidocaine/polymer mixture are graphically represented in FIG. 19.

Figure 20A:
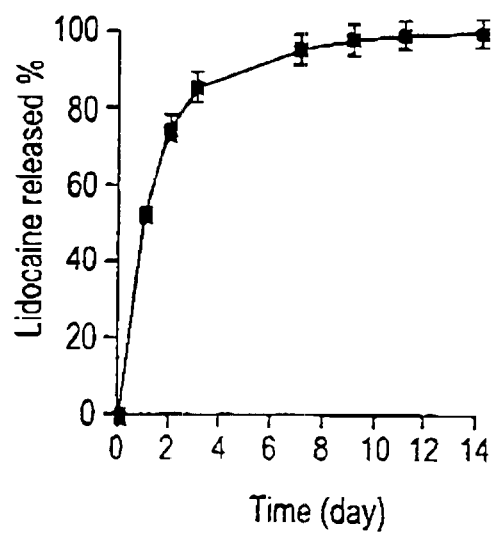
FIG. 20A shows the cumulative amount of lidocaine released in vitro as a function of incubation time.
Figure 20B:
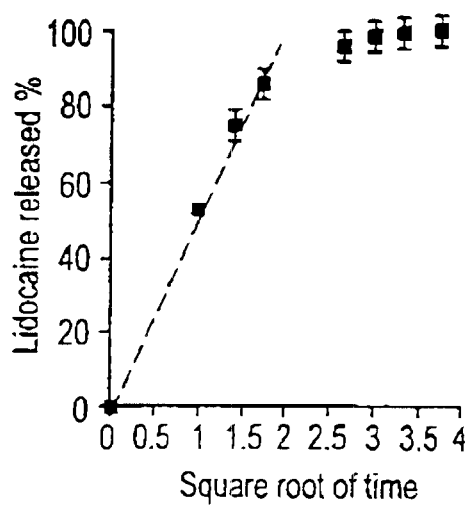
FIG. 20B shows lidocaine release as a function of the square root of time.

FIG. 20A displays the cumulative amount of lidocaine released as a function of incubation time and FIG. 20B shows the cumulative amount of lidocaine released over the square root of time, demonstrating that approximately 90% of the drug was released within one week. The linear relationship between the amount of lidocaine released and the square root of time indicated that the mechanism of drug release was mainly through diffusion during the test period.

Example 24

Release of Lidocaine from P(CHDM-HOP)in a Rat Sciatic Nerve Model In Vivo

Single jugular catheters were inserted into Male Sprague-Dawley rats, approximately 150–200 g in weight. The rats were anesthetized by i.p. injection with about 0.3–0.4 mL of an anesthetic cocktail (25 mg/mL ketamine, 2.5 mg/mL xylazine and 14.5% 200 proof ethanol). The sciatic nerve of the animal was identified. Each animal received a single injection of either 25 mg or 50 mg of lidocaine in either P(CHDM-HOP) or as a saline solution into its sciatic nerve to block the nerve. Control group rats received an equivalent amount of blank polymer injected into their sciatic nerves.

The rats were observed over time, and scores were assigned to both motor and nociceptive responses as follows:

Motor response and function
  normal motor function=0,
  slight foot drag=1,
  moderate foot drag=2, and
  no motor function=3;
Niciceltive response and function
  normal nociceptive response=0,
  slightly delayed nociceptive response=1,
  delayed nociceptive response =2, and
  no nociceptive response =3.

Blood samples were also collected at specific time points, and the plasma concentration of lidocaine was assayed by HLPC.

Figure 22:
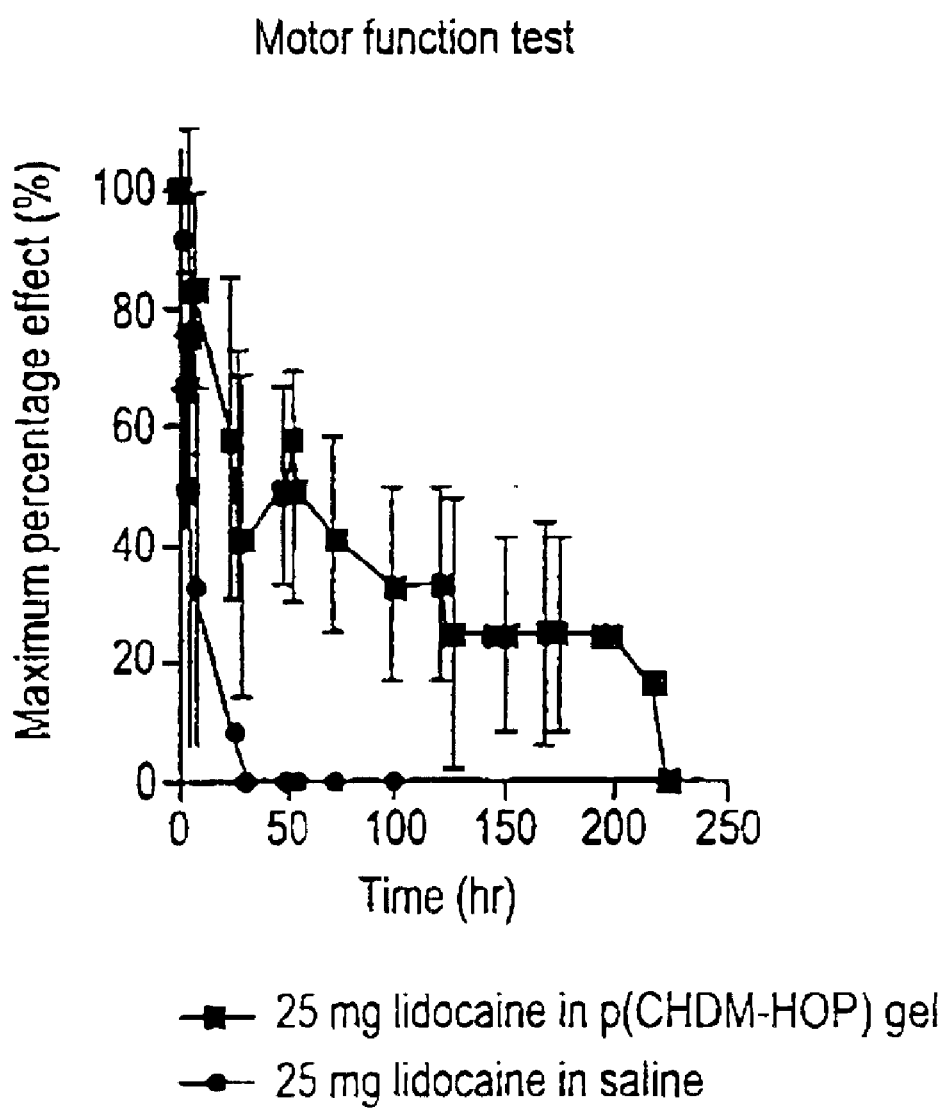
FIG. 22 plots the percentage of maximum motor function effect versus time after injection of 25 mg of lidocaine in P(CHDM-HOP) or in saline solution.

FIG. 22 shows the plot of percent of maximum motor function effect versus time after injection with 25 mg of lidocaine in P(CHDM-HOP) or in saline solution. A maximum percentage effect of 100% on this graph represents a score of "3" for "no motor response." All of the rats injected with lidocaine-containing preparations exhibited complete motor block during the first hour following injection. Table IV below summarizes the duration of the lidocaine blocking effects following injection of lidocaine in saline solution or in P(CHDM-HOP).

TABLE IV

Duration of Lidocaine Reaction Following Injection of Lidocaine in Saline Solution or P(CHDM-HOP)

| Lidocaine Formulation | Sensory Function | | Motor Function | |
|---|---|---|---|---|
| | Complete Block | Partial Block | Complete Block | Partial Block |
| Blank P(CHDM-HOP) | 0 | 0 | 0 | 0 |
| 25 mg Saline solution | 2 hrs | 48 hrs | 1 hr | 27 hrs |
| 25 mg in P(CHDM-HOP) | 54 hrs | 198 hrs | 1 hr | 198 hrs |
| 50 mg in P(CHDM-HOP) | 119 hrs | 265 hrs | 2 hrs | 240 hrs |

The duration of motor function blockage from the lidocaine in P(CHDM-HOP) was clearly longer than that achieved by the lidocaine saline solution. However, the extent of motor function blockage was only partial, in that a rat could still move its leg with a slight drag. It was also noted that the increase in complete motor blockage was minimal even at the higher lidocaine concentration of 50 mg of lidocaine.

Table V below shows the percentage of rats exhibiting complete blockage of the nociceptive response following the administration of 25 mg of lidocaine either as a saline solution or in P(CHDM-HOP).

TABLE V

Percentage of Rats with Complete Nociceptive Response

| | Percentage of Rats with Complete Block of Nociceptive Response | |
|---|---|---|
| Time | 25 mg Lidocaine in P(CHDM-HOP) | 25 mg Lidocaine in Saline Solution |
| 0.5 hrs | 100 | 100 |
| 3 hrs | 100 | 78 |
| 6 hrs | 100 | 50 |
| 24 hrs | 100 | 0 |
| 30 hrs | 78 | 0 |
| 48 hrs | 100 | 0 |
| 51 hrs | 100 | 0 |
| 54 hrs | 100 | 0 |
| 72 hrs | 78 | 0 |
| 99 hrs | 78 | 0 |
| 119 hrs | 50 | 0 |
| 125 hrs | 78 | 0 |
| 143 hrs | 50 | 0 |
| 149 hrs | 50 | 0 |

Compared with the lidocaine/saline solution, the lidocaine/P(CHDM-HOP) formulation prolonged the sensory blocking effect of lidocaine significantly.

Figure 21:
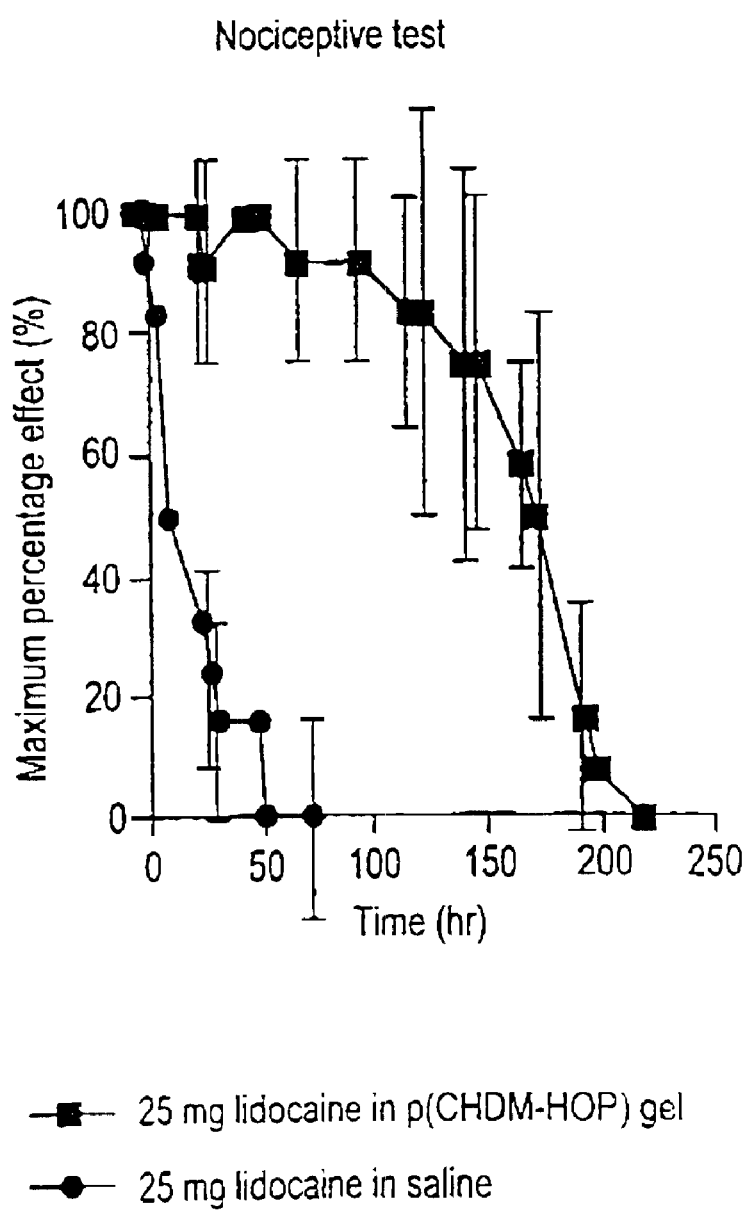
FIG. 21 plots the percentage of maximum nociceptive effect versus time after in vivo injection of 25 mg of lidocaine in P(CHDM-HOP) or in saline solution.

FIG. 21 plots the percentage of maximum nociceptive effect versus time after injection with 25 mg of lidocaine in either P(CHDM-HOP) or saline solution. The maximum percentage effect of 100% on this graph represented a score of "3", i.e., "no nociceptive response." Again, compared with the data from the lidocaine in saline solution, a significantly prolonged local anesthetic effect was observed in the lidocaine/P(CHDM-HOP) group.

It was noted that recovery from the motor block occurred well before complete recovery from the sensory block in both the lidocaine/saline solution and the lidocaine/P(CHDM-HOP) formulations. The rats could often move around with their hind limb and still exhibit no apparent response to pain stimuli. Because complete responsiveness to nociception was recovered well after the recovery of motor function, pharmaceutical compositions of the invention are believed to be well-suited for the clinical administration of local anesthetics and the management of chronic pain.

Figure 23:
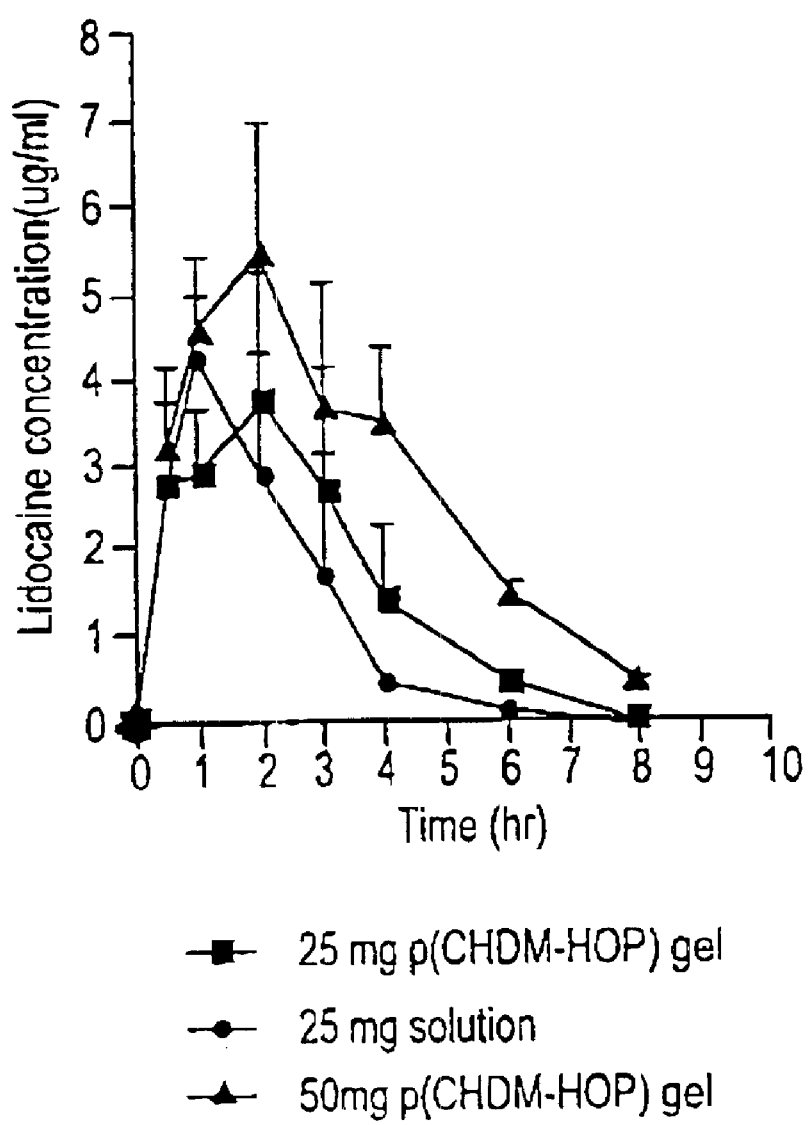
FIG. 23 shows the lidocaine concentration in plasma following injection of 25 mg of lidocaine in saline solution, of 25 mg of lidocaine in P(CHDM-HOP), and of 50 mg of lidocaine in P(CHDM-HOP).

FIG. 23 shows the lidocaine concentration in plasma following injection of 25 mg of lidocaine in saline solution, 25 mg of lidocaine in P(CHDM-HOP), and 50 mg of lidocaine in P(CHDM-HOP). By increasing the concentration of lidocaine in the polymer formulation, the duration of the anesthetic function was extended with a minimal increase in the lidocaine concentration in systemic circulation, indicating that diffusion of the majority of the drug was restricted to the local area.

The invention being thus described, it will be obvious that the same may be varied in many ways. Such variations are not to be regarded as a departure from the spirit and scope of at the invention, and all such modifications are intended to be a included within the scope of the following claims.

We claim:

1. A biodegradable, flowable or flexible polymer composition comprising (a) a polymer having the recurring monomeric units shown in formula I:

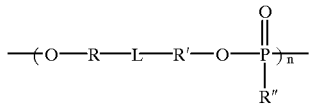

wherein:
- each of R and R' is independently straight or branched aliphatic, either unsubstituted or substituted with one or more non-interfering substituents;
- L is a divalent cycloaliphatic group, wherein the cyclic portion of said cycloaliphatic group is not aromatic or heterocyclic in nature;
- R" is selected from the group consisting of H, alkyl, alkoxy, aryl, aryloxy, heterocyclic or heterocycloxy; and
- n is 5 to 1,000; and (b) at least one biologically active substance, wherein said biodegradable polymer composition is biocompatible both before and upon biodegradation.

2. The polymer composition of claim 1 wherein each of R and R' is a branched or straight chain alkylene group having from one to seven carbon atoms.

3. The polymer composition of claim 1 wherein each of R and R' is a methylene group or an ethylene group.

4. The polymer composition of claim 1 wherein R" is an alkyl group, an alkoxy group, a phenyl group, a phenoxy group, or a heterocycloxy group.

5. The polymer composition of claim 1 wherein R" is an alkoxy group.

6. The polymer composition of claim 1 wherein n is 5 to 500.

7. The polymer composition of claim 1 wherein L is cyclohexylene.

8. The polymer composition of claim 1 wherein said polymer comprises additional biocompatible monomeric units or is blended with other biocompatible polymers.

9. The polymer composition of claim 1 wherein said composition also comprises at least one biologically active substance.

10. The polymer composition of claim 1 wherein said biologically active substance is selected from the group consisting of peptides, polypeptides, proteins, amino acids, polysaccharides, growth factors, hormones, anti-angiogenesis factors, interferons or cytokines, antigenic materials, and pro-drugs of these substances.

11. The polymer composition of claim 1 wherein said biologically active substance is a therapeutic drug or pro-drug.

12. The polymer composition of claim 11 wherein said drug is selected from the group consisting of anti-neoplastic agents, local anesthetics, antibiotics, anti-virals, anti-fungals, anti-inflammatories, anticoagulants, antigenic materials suitable for vaccine applications, and pro-drugs of these substances.

13. The polymer composition of claim 1 wherein said polymer composition is non-toxic and results in minimal tissue irritation when injected or is otherwise placed into intimate contact with vasculated tissues.

14. A biodegradable, flowable or flexible polymer composition comprising a polymer having the recurring monomeric units shown in formula I:

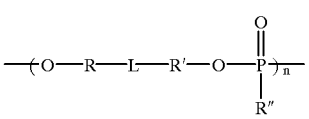

wherein:
- each of R and R' is independently straight or branched aliphatic, either unsubstituted or substituted with one or more non-interfering substituents;
- L is a divalent cycloaliphatic group, wherein the cyclic portion of said cycloaliphatic group is not aromatic or heterocyclic in nature;
- R" is selected from the group consisting of H, alkyl, alkoxy, aryl, aryloxy, heterocyclic or heterocycloxy; and
- n is 5 to 1,000,
- or alternatively one or more of R, R' and R" is a biologically active substance in a form capable of being released in a physiological environment;

wherein said biodegradable polymer composition is biocompatible both before and upon biodegradation.

15. The polymer composition of claim 14 wherein each of R and R' is a branched or straight chain alkylene group having from one to seven carbon atoms.

16. The polymer composition of claim 14 wherein each of R and R' is a methylene group or an ethylene group.

17. The polymer composition of claim 14 wherein R" is an alkyl group, an alkoxy group, a phenyl group, a phenoxy group, or a heterocycloxy group.

18. The polymer composition of claim 14 wherein R" is an alkoxy group.

19. The polymer composition of claim 14 wherein n is 5 to 500.

20. The polymer composition of claim 14 wherein L is cyclohexylene.

21. The polymer composition of claim 14 wherein said polymer comprises additional biocompatible monomeric units or is blended with other biocompatible polymers.

22. The polymer composition of claim 14 wherein R" is a biologically active substance.

23. The polymer composition of claim 14 wherein either R or R' is a biologically active substance.

24. The polymer composition of claim 14 wherein said biologically active substance is selected from the group consisting of peptides, polypeptides, proteins, amino acids, polysaccharides, growth factors, hormones, anti-angiogenesis factors, interferons or cytokines, antigenic materials, and pro-drugs of these substances.

25. The polymer composition of claim 14 wherein said biologically active substance is a therapeutic drug or pro-drug.

26. The polymer composition of claim 25 wherein said drug is selected from the group consisting of anti-neoplastic agents, local anesthetics, antibiotics, anti-virals, anti-fungals, anti-inflammatories, anticoagulants, antigenic materials suitable for vaccine applications, and pro-drugs of these substances.

27. The polymer composition of claim 14 wherein said polymer composition is non-toxic and results in minimal tissue irritation when injected or is otherwise placed into intimate contact with vasculated tissues.

28. The polymer composition of claim 11 wherein said drug is selected from the group consisting of β-adrenergic blocking agents, anabolic agents, androgenic steroids, antacids, anti-asthmatic agents, anti-allergenic materials, anti-arrhythmics, anti-cholesterolemic and anti-lipid agents, anti-cholinergics and sympathomimetics, anti-convulsants, anti-diarrheals, anti-emetics, anti-hypertensive agents, anti-infective agents, anti-malarials, anti-manic agents, anti-nauseants, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, humoral agents, hyperglycemic agents, hypnotics, hypoglycemic agents, ion exchange agents, laxatives, mineral supplements, miotics, mucolytic agents, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, and pro-drugs of these substances.

29. The polymer composition of claim 25 wherein said drug is selected from the group consisting of β-adrenergic blocking agents, anabolic agents, androgenic steroids, antacids, anti-asthmatic agents, anti-allergenic materials, anti-arrhythmics, anti-cholesterolemic and anti-lipid agents, anti-cholinergics and sympathomimetics, anti-convulsants, anti-diarrheals, anti-emetics, anti-hypertensive agents, anti-infective agents, anti-malarials, anti-manic agents, anti-nauseants, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, humoral agents, hyperglycemic agents, hypnotics, hypoglycemic agents, ion exchange agents, laxatives, mineral supplements, miotics, mucolytic agents, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, and pro-drugs of these substances.

30. The polymer composition of claim 1, wherein said biologically active substance is lidocaine.

31. The polymer composition of claim 1, wherein said biologically active substance is paclitaxel.

32. The polymer composition of claim 14, wherein said biologically active substance is lidocaine.

33. The polymer composition of claim 14, wherein said biologically active substance is paclitaxel.

* * * * *